US012600988B2

(12) United States Patent
Qin et al.

(10) Patent No.: US 12,600,988 B2
(45) Date of Patent: Apr. 14, 2026

(54) CORONAVIRUS PSEUDOVIRUS PACKAGING SYSTEM, PACKAGING METHOD THEREFOR, AND APPLICATION OF CORONAVIRUS PSEUDOVIRUS IN EVALUATING DISINFECTION EFFICACY

(71) Applicant: FANTASIA BIOPHARMA (ZHEJIANG) CO. LTD, Jinhua (CN)

(72) Inventors: Frank Xiaofeng Qin, Jinhua (CN); Zhiming Wei, Jinhua (CN); Limei Long, Jinhua (CN); Renxiang Yang, Jinhua (CN); Fan Li, Jinhua (CN)

(73) Assignee: FANTASIA BIOPHARMA (ZHEJIANG) CO. LTD, Jinhua (CN)

( * ) Notice: Subject to any disclaimer, the term of this patent is extended or adjusted under 35 U.S.C. 154(b) by 789 days.

(21) Appl. No.: 18/010,885

(22) PCT Filed: Jun. 15, 2021

(86) PCT No.: PCT/CN2021/100164
§ 371 (c)(1),
(2) Date: Jun. 16, 2023

(87) PCT Pub. No.: WO2021/254341
PCT Pub. Date: Dec. 23, 2021

(65) Prior Publication Data
US 2023/0332177 A1     Oct. 19, 2023

(30) Foreign Application Priority Data

Jun. 16, 2020   (CN) .......................... 202010545785.6
Jan. 22, 2021   (CN) .......................... 202110089069.6

(51) Int. Cl.
| | |
|---|---|
| *C12N 15/86* | (2006.01) |
| *A01N 63/40* | (2020.01) |
| *A01P 1/00* | (2006.01) |
| *C07K 14/005* | (2006.01) |
| *C12N 7/00* | (2006.01) |
| *C12N 15/65* | (2006.01) |

(52) U.S. Cl.
CPC ............. *C12N 15/86* (2013.01); *A01N 63/40* (2020.01); *A01P 1/00* (2021.08); *C12N 2740/15043* (2013.01); *C12N 2760/20242* (2013.01); *C12N 2770/20041* (2013.01)

(58) Field of Classification Search
None
See application file for complete search history.

(56) References Cited

U.S. PATENT DOCUMENTS

| | | |
|---|---|---|
| 10,906,942 B2 | 2/2021 | Ebert et al. |
| 2019/0153039 A1 | 5/2019 | Ebert et al. |
| 2020/0297782 A1 * | 9/2020 | Ambrogio .............. A01N 63/20 |
| 2021/0221851 A1 | 7/2021 | Ebert et al. |

FOREIGN PATENT DOCUMENTS

| | | | |
|---|---|---|---|
| AU | 2003268505 A1 | 3/2004 | |
| CA | 2498297 A1 | 3/2004 | |
| CN | 1552851 A | 12/2004 | |
| CN | 1820078 A | 8/2006 | |
| CN | 102653781 A | 9/2012 | |
| CN | 109312366 A | 2/2019 | |
| CN | 111088283 A | 5/2020 | |
| CN | 111593073 A | 8/2020 | |
| CN | 111603557 A | 9/2020 | |
| CN | 111893097 A | 11/2020 | |
| CN | 112760297 A | 5/2021 | |
| EP | 1 549 756 A2 | 7/2005 | |
| EP | 3 246 410 A1 | 11/2017 | |
| EP | 3 458 594 B1 | 3/2021 | |
| JP | 2005-537802 A | 12/2005 | |
| JP | 2019-516374 A | 6/2019 | |
| JP | 6996756 B2 | 2/2022 | |
| TW | 200418982 A | 10/2004 | |
| WO | 2004/022716 A2 | 3/2004 | |
| WO | 2017/19877 A1 | 2/2017 | |
| WO | WO-2020029274 A1 * | 2/2020 | .............. C12P 21/02 |
| WO | 2021/185310 A1 | 9/2021 | |

OTHER PUBLICATIONS

Sep. 23, 2021 International Search Report issued in International Patent Application No. PCT/CN2021/100164.
Giroglou et al., "Retroviral Vectors Pseudotyped with Severe Acute Respiratory Syndrome Coronavirus S Protein", Journal of Virology, vol. 78, No. 17, Sep. 2004, pp. 9007-9015.
Liu et al., "A recombinant VSV-vectored MERS-CoV vaccine induces neutralizing antibody and T cell responses in rhesus monkeys after single dose immunization", Antiviral Research, vol. 150, 2018, pp. 30-38.
Rentsch et al., "A Vesicular Stomatitis Virus Replicon-Based Bioassay for the Rapid and Sensitive Determination of Multi-Species Type I Interferon", PLoSONE, vol. 6, Issue 10, Oct. 2011, pp. 1-6.

(Continued)

*Primary Examiner* — Anna Skibinsky
*Assistant Examiner* — Catherine L Mccormick
(74) *Attorney, Agent, or Firm* — OLIFF PLC.

(57)     ABSTRACT

A packaging system for a coronavirus pseudovirus, including a vesicular stomatitis virus (VSV) vector in which Fluc and EGFP dual-reporter genes replace a GP gene, and packaging cell that expresses a coronavirus spike protein. The packaging system may quickly package pseudoviruses by using a one-step packaging method, and may be used in the research of coronaviruses such as COVID-19 (SARS-CoV-2), SARS (SARS-CoV) and MERS, and other viruses. The packaging system and thereby pseudovirus method may also be used to evaluate the efficacy of disinfectants by means of virus contamination distribution models, setting up scenarios, and sampling and testing steps.

10 Claims, 10 Drawing Sheets

Specification includes a Sequence Listing.

(56) References Cited

OTHER PUBLICATIONS

Fukushi et al., "Vesicular stomatitis virus pseudotyped with severe acute respiratory syndrome coronavirus spike protein", Journal of General Virology, vol. 86, pp. 2269-2274.

Nie et al., "Establishment and validation of a pseudovirus neutralization assay for SARS-CoV-2", Emerging Microbes & Infections, vol. 9, 2020, pp. 680-686.

"Genbank Accession No. AAX16192.1" Genbank, Mar. 25, 2009.

* cited by examiner

M: Marker
1: COVID-19-S
2: COVID-19-S-C19
3: COVID-19-S-C19HA
4: COVID-19-S-C27
5: COVID-19-S-C53
6: SARS-CoV-S-C19
7: MERS-CoV-S-C19
8: VSVG Disinfecting Results of Ozone for COVID-19 pseudovirus at room temperature Disinfecting Results of Ozone for COVID-19 pseudovirus at -20℃

1

CORONAVIRUS PSEUDOVIRUS PACKAGING SYSTEM, PACKAGING METHOD THEREFOR, AND APPLICATION OF CORONAVIRUS PSEUDOVIRUS IN EVALUATING DISINFECTION EFFICACY

The present application contains a Sequence Listing that has been submitted electronically in ASCII format and is hereby incorporated by reference in its entirety. The ASCII copy, created on Jun. 16, 2023, is named Substitute Sequence Listing_ST25.txt and is 71,623 bytes in size.

TECHNICAL FIELD

This disclosure relates to the field of gene and cell engineering and virology, and in particular, to a pseudovirus packaging vector and a packaging cell system. The pseudovirus packaging vector and the packaging system may be used for preparing a coronavirus pseudovirus by a one-step packaging method, and the prepared coronavirus pseudovirus may be used as a biological indicator for detection and evaluation of efficacy of a biological and chemical substance and a physical treatment method for inhibiting and disinfecting coronavirus.

BACKGROUND

COVID-19 is a coronavirus that can cause fatal pneumonia in humans. In addition to COVID-19, two other coronaviruses, severe acute respiratory syndrome coronavirus (SARS-CoV) and Middle East respiratory syndrome coronavirus (MERS-CoV), also have caused fatal pneumonia in humans since the early 21st century. In addition, four low-pathogenic coronaviruses are also prevalent in humans: HCoV-OC43, HCoV-HKU1, HCoV-NL63, and HCoV-229E. Local cases of COVID-19 infection have been confirmed in many places in China. It has been confirmed that transmission of COVID-19 can occur frequently through cold chain logistics processes. In accordance with the COVID-19 Prevention and Control Plan issued by the State Council of RPC, all local governments are required to take protection actions for people engaged in cold-chain food operations. Cutting off transmission of COVID-19 through cold chain logistics processes directly affects China's overall coordinated approach to the decisions of epidemic control as well as strengthening of the strategy of "preventing the coronavirus from re-entering the country to cause a new epidemic".

Virus inactivation, a conventional technology, may be simply divided into physical inactivation and chemical inactivation, based on the principle thereof. Although there is a variety of common virucidal disinfectants such as ozone, ultraviolet light, chlorine dioxide, peracetic acid, hydrogen peroxide, sodium dichloroisocyanurate, irradiation, negative ions, such virucidal disinfectants have inconsistent capability of virus inactivation, and application ranges of such virucidal disinfectants have no data support, mainly because there is no unified and effective method for evaluating capability of a virucidal disinfectant for virus inactivation. Particularly, for SARS-CoV-2, SARS-CoV, MERS-CoV and other highly transmissible and harmful viruses, evaluation of live viruses may only be carried out in a P3 laboratory. The lack of test and evaluation methods with biological safety directly leads to the lack of evaluation support for suitable new technologies or applications such as ozone and irradiation, which further makes it hard to determine parameters and applicable rules of the technologies, as well as promotion and application of the technologies.

The known pseudovirus refers to a replication-defective virus that is capable of integrating an envelope glycoprotein of another different virus to form a virus with the envelope of the exogenous virus, while its genome keeps the genomic characteristics of the original virus vector itself. Pseudoviruses have lost their replication capability due to genetic defect in their genome, only capable of single-cycle infection, thus have high biological safety. Therefore, the pseudovirus approach can provide a safe and effective research method for studying viruses that are highly pathogenic, highly infectious, or hard to be cultured in vitro, such as SARS-CoV-2. Furthermore, pseudoviruses constructed in vitro also have advantages such as high stability and wide host tropism, so they are widely used in research, development, and evaluation of vaccines; detection, screening, and evaluation of neutralizing antibodies; discovery of antigenic epitopes of neutralizing antibodies; research and development of antibodies, macromolecule and small-molecule drugs to inhibit virus invasion, as well as physically virucidal disinfection methods and chemical virucidal disinfectants.

It is of great significance to package and prepare pseudoviruses having no potential biosafety hazards for SARS-CoV-2, SARS-CoV, MERS-CoV, and the like, and to apply them to examine and evaluate virus neutralization and inhibition capability, as well as the performance and efficacy of virucidal disinfectants in virus inactivation.

SUMMARY

It is safe and effective to use pseudoviruses that are replication-defective and unable to produce infectious progeny to simulate a process of a wild virus infecting a host. Packaging of VSV occurs on the cell membrane and involves virion budding from the cell surface. During the budding, VSV acquires an envelope formed by a bilayer lipid from the cell membrane and a trimer of VSV glycoprotein (VSV-G). When VSV-G genes are partially or completely replaced by dual-reporter genes, and an envelope protein of an exogenous virus is fully expressed in dVSVΔG-infected cells, the exogenous virus glycoprotein can be assembled onto the envelope of VSV virus particles. In this study, we compared pseudoviruses packaged with the full-length COVID-19 S protein (COVID-19-S), C-terminal truncated S protein (C19-HA), and S protein with 19aa truncated at C-terminal and fused with HA (C19-HA) dVSVΔG-COVID-19-S-C19-HA. It is found that pseudovirus dVSVΔG-COVID-19-S-C19-HA has a much higher infection efficiency than that of dVSVΔG-COVID-19-S, and also significantly higher than that of dVSVΔG-COVID-19-S-C19. In addition, 293T-hACE2 cells stably expressing human ACE2 (hACE2) are most sensitive to pseudovirus infection. In contrast, Vero-E6 has moderate infection efficiency, while 293 T cells are completely insensitive to COVID-19 pseudoviruses. Based on dVSVΔG-COVID-19-S-C19-HA and 293T-hACE2 cells, methods for detection and evaluation of efficacy of biological, chemicals and physical treatment methods for inhibiting and disinfecting coronavirus (including evaluation of efficacy of ozone in disinfecting coronavirus in cold chain environment), and evaluation of neutralization activity of antibodies in serum samples after immunization with various coronavirus vaccines are established. This method system can be used for the research of coronavirus such as COVID-19 (SARS-CoV-2), SARS (SARS-CoV), MERS, and the like.

A coronavirus pseudovirus packaging system comprises a safe and efficient modified vesicular stomatitis virus (VSV), and an packaging cell that expresses coronavirus spike protein; wherein the modified vesicular stomatitis virus VSV is defined as a replication-defective virus with GP gene partially or completely replaced by Fluc and EGFP dual-reporter genes, and the modified vesicular stomatitis virus VSV is named as dVSVΔG-Fluc-EGFP.

Preferably, in the coronavirus pseudovirus packaging system, the dual-reporter genes include a fluorescent protein reporter gene and a luciferase reporter gene, and the fluorescent protein reporter gene is selected from a reporter gene corresponding to green fluorescent protein or red fluorescent protein; and the luciferase reporter gene is selected from a reporter gene corresponding to firefly luciferase or renilla luciferase.

Preferably, in the coronavirus pseudovirus packaging system, the fluorescent protein reporter gene is an enhanced green fluorescent protein (EGFP) gene, and the corresponding gene sequence is set forth in SEQ ID NO: 1; the luciferase reporter gene is selected from firefly luciferase Fluc gene with optimized codons, and the sequence of the firefly luciferase Fluc gene is set forth in SEQ ID NO: 2.

Preferably, in the coronavirus pseudovirus packaging system, the gene encoding GP in the genetic material of dVSVΔG-Fluc-EGFP is replaced by the Fluc reporter gene, the EGFP reporter gene is integrated between Fluc and VSV polymerase L gene, and the gene sequence of dVSVΔG-Fluc-EGFP is set forth in SEQ ID NO: 3.

Preferably, in the coronavirus pseudovirus packaging system, the packaging cell is selected from 293T, the packaging cell transiently or stably or inductively expresses the coronavirus spike protein, the transient expression is realized by transfecting the cell with an eukaryotic expression vector, the stable expression is realized by transducing the cell with a lentiviral vector system, and the corresponding induced expression is realized by transducing the cell with a tetracycline-regulated tet-on/off vector system.

Preferably, in the coronavirus pseudovirus packaging system, the envelope protein expressed by the packaging cell corresponds to the S gene in the coronaviruses SARS, MERS or COVID-19, and the SARS coronavirus envelope protein is selected from a sequence obtained after deletion of 19 amino acids at 3' end of the SARS coronavirus spike protein, namely a sequence of SEQ ID NO: 4; the MERS coronavirus envelope protein is selected from a sequence obtained after deletion of 19 amino acids at 3' end of the MERS coronavirus spike protein, namely a sequence of SEQ ID NO: 5; the COVID-19 coronavirus envelope protein is selected from a sequence obtained after deletion of 19 amino acids at 3' end of the COVID-19 coronavirus spike protein, namely a sequence of SEQ ID NO: 6, or the COVID-19 coronavirus envelope protein is selected from a sequence obtained after deletion of 19 amino acids at 3' end of the COVID-19 coronavirus spike protein and fusion of HA protein, namely a sequence of SEQ ID NO: 7; the envelope protein expression expressed by the packaging cell is mediated by transient expression plasmid or stable expression plasmid or stable and inducible expression lentivirus vector, including eukaryotic expression vector, and four plasmids transiently expressing the envelope protein in the packaging cell are named as expression plasmids pCA-SARS-C19, pCA-MERS-C19, pCA-COVID-19-C19, and pCA-COVID-19-C19-HA, respectively, as well as derivative vector expressing the same encoded protein. Preferably, the target to be fused after deletion of 19aa at the 3' end of S in the S-C19-HA is not limited to HA, but may be other peptides with labeling function such as flag, myc, and his.

A one-step packaging method for a pseudovirus packaging system, wherein the pseudovirus packaging system includes dVSVΔG-Fluc-EGFP and an packaging cell that expresses the coronavirus spike protein, wherein the surface of dVSVΔG-Fluc-EGFP is assembled with complete GP envelope protein, GP gene in genetic material is partially or completely replaced by Fluc and EGFP dual-reporter genes, the expression of the coronavirus spike protein is mediated by pCAGGS, the coronavirus spike protein is selected from a truncate of 16aa-28aa at 3' end of the S gene, and dVSVΔG-Fluc-EGFP and the packaging cell that expresses the coronavirus spike protein are mixed in one step, and supernatant is collected after a certain time to obtain the coronavirus pseudovirus. Preferably, the coronavirus spike protein performs best when it is selected from a truncate of 19aa at 3' end of the S gene.

Preferably, the one-step packaging method includes the following steps:

(1) adding dVSVΔG-Fluc-EGFP to 293T cell that transiently or stably or inductively expresses VSV envelope protein GP, collecting supernatant after 24 h to obtain the amplified VSV replication-defective virus, and measuring its titer; and (2) passaging the packaging cell 293T that transiently or stably or inductively expresses the coronavirus spike protein into a 60 mm dish, adding dVSVΔG-Fluc-EGFP, wherein multiplicity of infection (MOI) is 0.1 to 5, culturing in an incubator at 32° C. to 37° C., harvesting pseudovirus supernatant after 24 h, then treating with anti-VSV neutralizing antibody for 2 h, and filtering with 0.22 um filter membrane to obtain the coronavirus pseudovirus.

An additional pseudovirus packaging system comprises modified vesicular stomatitis virus VSV, an packaging cell that expresses spike protein of an additional virus; wherein the modified vesicular stomatitis virus VSV is defined as a VSV replication-defective virus with GP gene partially or completely replaced by Fluc and EGFP dual-reporter genes, and the VSV replication-defective virus is named as dVSVΔG-Fluc-EGFP. The transiently expressed or stably expressed or inductively expressed packaging plasmid and vector express an envelope protein of a target virus in an packaging cell, and the envelope protein expressed at the cell level by the transiently expressed or stably expressed or inductively expressed packaging plasmid and vector is selected from one or more of coronavirus, herpesvirus, rhabdovirus, poxvirus, hepadnavirus, filovirus, rhabdovirus, influenza virus, paramyxovirus, flavivirus, paramyxovirus, flavivirus, enveloped virus, bunyavirus, or retrovirus.

Preferably, in the additional pseudovirus packaging system, the coronavirus is COVID-19 (SARS-CoV-2), SARS (SARS-CoV), MERS (MERS-CoV), HCoV-OC43, HCoV-HKU1, HCOV-NL63, or HCoV-229E; the hepadnavirus is hepatitis B virus or hepatitis C virus; the filovirus is Ebola virus; the rhabdovirus is rabies virus; the paramyxovirus is measles virus or respiratory syncytial virus; and the flavivirus is Zika virus or dengue virus.

Preferably, the additional pseudovirus packaging system includes dVSVΔG-Fluc-EGFP and the packaging cell, and the packaging cell is selected from 293, 293T, 293sus, HEK293, HEK293T, HEK293FT, BHK, or Vero with high transfection efficiency and good stability. That is, the pseudovirus packaging system of this disclosure may be applied to a variety of viruses other than those described in detail herein, and may be widely applied to preparation of pseudoviruses for other virus types.

The coronavirus pseudoviruses packaged by the above coronavirus pseudovirus packaging system may be used as a biological indicator to replace a wild-type coronavirus for detection and evaluation of efficacy of biological and chemical substances and physical treatment methods for inhibiting and disinfecting the coronavirus, wherein the substances and the methods for inhibiting and disinfecting the coronavirus include an anti-coronavirus neutralizing antibody and medicament, chemical virucidal disinfectants and physical virucidal disinfection means.

Use of a coronavirus pseudovirus in evaluation of efficacy of a virucidal disinfectant, comprises the following steps:

(1) construction of a virus-contaminated environment simulating distribution of a target virus under a virucidal disinfectant evaluation scenario, including the existence of medium, temperature, humidity and gas disturbance, through analysis of virus contamination distribution models;

diluting the packaged coronavirus pseudovirus, uniformly smearing the diluted coronavirus pseudovirus on a medium, and setting environmental parameters of the evaluation scenarios;

(2) determination of coronavirus pseudovirus concentration before virucidal disinfection treatment based on the evaluation requirements, performing standard virus characteristic detection before treatment by sampling the coronavirus pseudovirus at different positions and different points; and (3) sampling and determination during and after virucidal disinfection treatment uniformly spraying or smearing the virucidal disinfectant on the medium;

based on the evaluation requirements, at the positions and points selected in the step (2), sampling the coronavirus pseudovirus at different times, and detecting titer activity of the coronavirus pseudovirus.

Preferably, the use of the coronavirus pseudovirus in evaluation of the efficacy of the virucidal disinfectant is characterized in that the virus-contaminated environment in the step (1) includes a logistics environment (such as a cold-chain logistics environment), a home environment, a public place, a school environment and the like.

Preferably, the use of the coronavirus pseudovirus in evaluation of the efficacy of the virucidal disinfectant is characterized in that multiple experimental groups may be constructed in the step (1) to avoid excessive errors, and the step (3) includes observing the expression of fluorescent protein and luciferase after 293T-hACE2 is infected by the pseudovirus for measurement and calculation of infection capacity and bioactivity titer (PFU/ml) of the pseudovirus as well as detection of copy number of the pseudovirus nucleic acid.

Preferably, the use of the coronavirus pseudovirus in evaluation of the efficacy of the virucidal disinfectant is characterized in that the virucidal disinfectant (peroxides, quaternary ammonium salts, chlorine-containing compounds, and alcohols) and the physical treatment method in the step (3) includes various combinations of one or more of ozone, peroxyacetic acid, hydrogen peroxide, chlorine dioxide, oxydol, sodium dichloroisocyanurate, ultraviolet light, negative ions, irradiation, or the like.

Preferably, the use of the coronavirus pseudovirus in evaluation of the efficacy of the virucidal disinfectant is characterized in that the medium in the step (1) or step (3)

includes one or more of plastic, foam, bookbinding paperboard, boxboard, textile, or metal foil.

By using the packaging system and the packaging method of this disclosure, pseudoviruses of various viruses with envelope proteins can be packaged, and these pseudoviruses, in a one-to-one correspondence with the viruses, can be safely, quickly and accurately used for detection and evaluation of efficacy of biological and chemical substances and physical treatment methods used for inhibiting and disinfecting coronavirus. The coronavirus pseudovirus of this disclosure can rapidly package a pseudovirus with single-cycle infection, low background signal and high titer, and has characteristics of rapid detection and simple and convenient operation compared with a lentivirus-based pseudovirus system. The pseudovirus packaging system of this disclosure has universal extendibility, is not limited to the coronavirus specifically described herein, but also can be extended to other types of viruses, and the one-step packaging method of the corresponding pseudovirus packaging system can also be applied to one-step packaging methods for other types of pseudoviruses.

The pseudovirus (not limited to coronavirus pseudovirus) packaged by the above packaging system and the packaging method may be used for detection and evaluation of efficacy of biological and chemical substances and physical treatment methods for inhibiting and disinfecting corresponding viruses. This disclosure has the following beneficial effects: (1) through optimal combination and design on the use environment and dosage of the detected substances and methods for inhibiting and disinfecting the coronavirus, the virus inactivation function of the detected substances and methods for inhibiting and disinfecting the coronavirus can be accurately, visually, qualitatively or quantitatively compared and verified; (2) the pseudovirus reporting system biological indicator in this disclosure has high biological safety, can simulate the transmission and pathogenic characteristics of various viruses, and can meet the requirements for evaluating the virus inactivation ability of different substances and methods for inhibiting and disinfecting viruses in conventional biosafety environment; (3) the pseudovirus fluorescent reporter gene in this disclosure can intuitively reflect the virus inactivation results of the detected substances and methods for inhibiting and disinfecting viruses; and (4) the use of this disclosure greatly promotes research and development of substances and methods for inhibiting and disinfecting viruses and studying the blocking effect on cold chain transmission, and provides practical and feasible favorable conditions.

Figures 1, 2:
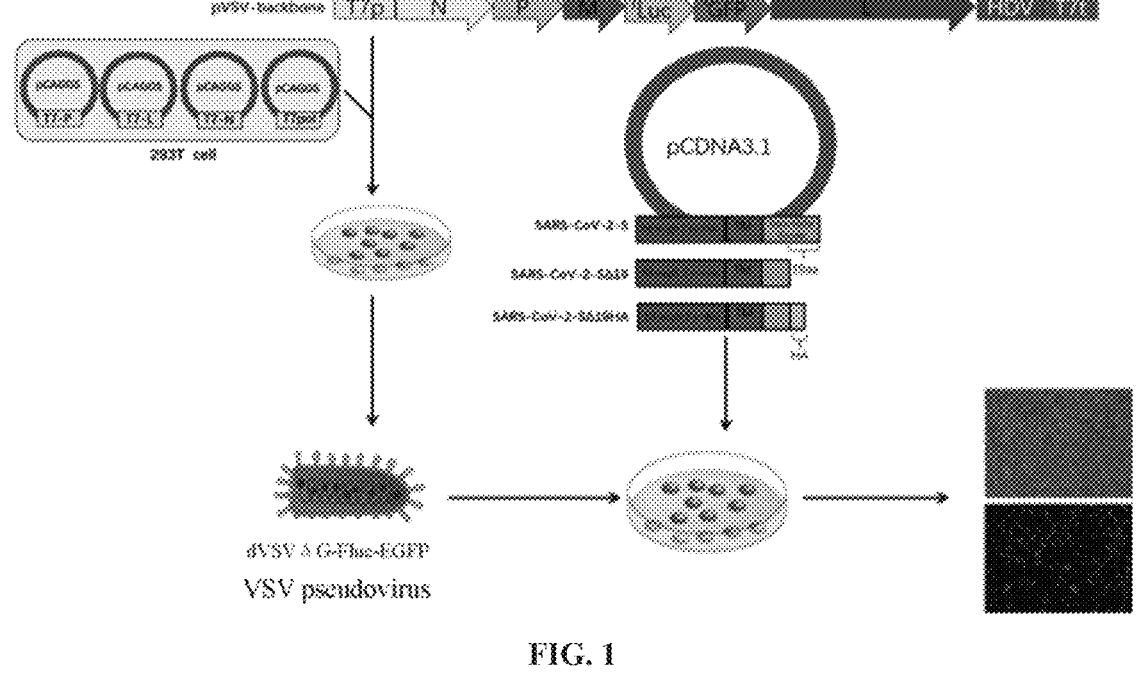
FIG. 1 shows a construction schematic diagram of dVSVΔG-Fluc-EGFP-based pseudovirus.
FIG. 2 shows construction of COVID-19/SARS/MERS-S expression plasmid.

COVID19 in the figures represents COVID-19.

DETAILED DESCRIPTION

In the following, this disclosure will be further described in detail with reference to specific examples, which are intended for explanation but not limitation of this disclosure. This disclosure mainly relates to integrating the genes of COVID-19-S, SARS-CoV-S, and MERS-S or truncated sequences thereof into an expression system, and further integrating VSV pseudovirus of the envelope antigen through the constructed dVSVΔG-EGFP-FLuc dual-reporter packaging system, and is used for detecting production of neutralizing antibodies in immune serum obtained after the relevant antigen protein is immunized in mice.

The reagents and consumables used in this disclosure are as follows: Lipofectamine LTX (Invitrogen 15338100), PBS (Hyclone SH30256.01), DMEM high glucose medium (Gibco C11995500), Penicillin-Streptomycin (Gibco 15140-122), fetal bovine serum (Gibco 10091-148), Opti-MEM® I Reduced Serum Medium (Gibco 31985-070), 96-well cell culture plate (Corning 3599), 6-well cell culture plate (Corning 3516), 6-cm cell culture plate (Corning 430166), COVID-19 RBD protein (Genescript Biotechnology Ltd Z03485), COVID-19 S1 protein (Genescript Biotechnology Ltd Z03485), SARS-CoV S RBD protein (Sino Biological 40150-V08B2), and MERS-CoV S1 protein (Sino Biological 40069-V08B1).

Cell Line:

Vero-E6 (ATCC, CRL-1586), 293T (ATCC-derived) cells were maintained in a high glucose DMEM (SIGMA-AL-DRICH) and supplemented with 10% LBS (Gibco), penicillin (100 IU/mL), and streptomycin (100 μg/mL), passaged every 2 days in 5% carbon dioxide atmosphere at 37° C., infected with lentivirus expressing hACE2 for 72 hours, and screened for purinomycin resistance to obtain 293T-hACE2 cells.

Antibody Preparation:

Balb/C mice were immunized with COVID-19 spike protein (RBD/S1), SARS-CoV S RBD, and MERS-CoV S1 at 50 μg/mouse every other week. Complete adjuvant was added to the primary immunization, and incomplete adjuvant was added to the subsequent booster immunization to prepare specific polyclonal antibody against spike proteins of COVID-19, SARS-CoV and MERS-CoV, and activity of neutralizing antibody was identified.

Construction of Different Modified Envelope Expression Vectors:

Molecular construction: After codon optimization focusing on Spike protein (S protein) clone of COVID-19, full-length sequence of S (1-3822 bp), a sequence of S with 19 amino acids deleted from C-terminal (1-3765 bp), a sequence of S with 19 amino acids deleted from C-terminal plus HA tag (1-3792 bp), a sequence of S with 27 amino acids deleted from C-terminal (1-3735 bp), and a sequence of S with 53 amino acids deleted from C-terminal (1-3663 bp) were cloned into pCAGGS vector, respectively. For SARS-CoV and MERS-CoV, sequences of S with 19 amino acids deleted from C-terminal were selected as the first choice.

Example 1 Construction of Different Type of
Envelope Plasmids

The S gene sequence published according to NCBI was codon optimized to facilitate the expression in cells. The sequence was respectively synthesized on a pCDNA3.1 vector by GenScript Biotech Corporation. After the target gene was amplified by PCR, the target band was recovered and purified by a fragment purification kit. The fragment and pCAGGS vector were digested with restriction endonucleases MCS1 (Xhol) and MCS2 (Nhel) at 37° C. for 3 h. The vector and the target fragment were recovered from gel, subjected to ligation reaction, and then transformed into competent cells. The positive clones were screened by colony PCR, the plasmid construction was verified by enzyme digestion and sequencing. The specific steps were as follows: 1. Primer synthesis and primer information: the primers were synthesized by GENEWIZ, Inc., and the PCR primers selected for construction and amplification of COVID-19-S gene are shown in Table 1.

TABLE 1

| Primers for amplification and detection of COVID-19-S gene | | | | |
|---|---|---|---|---|
| Product No. | Product size | Primer No. | Primer sequence (5'-3') | Description |
| COVID19-S | 3822bp | COVID19-S-Xho1-F1 | CCGCTCGAGATGTTCGTG TTTCTGGTG (SEQ ID NO: 8) | Upstream primer for cloning full-length S gene |
| | | COVID19-S-Nhe1-R1 | CTAGCTAGCTTAGGTGTA GTGCAGCTTCAC (SEQ ID NO: 9) | Downstream primer for cloning full-length S gene |

Note: The underline represents the digestion site.

1.1 The selected PCR primers and Colony PCR primers for amplification of COVID-19-S-C19 gene are shown in Table. 2:

[0057] Table 2 COVID-19-S-C19 gene amplification

| Product No. | Product size | Primer No. | Primer sequence (5'-3') | Description |
|---|---|---|---|---|
| COVID19-S-C19 | 3765bp | COVID19-S-C19-Xho1-F1 | CCGCTCGAGATGTTCGTGT TTCTGGTG (SEQ ID NO: 10) | Upstream primer for cloning COVID19-S-C19 gene |
| | | COVID19-S-C19-Nhe1-R1 | CTAGCTAGCTTAACAGCA GCTTCCACAAGAACA (SEQ ID NO: 11) | Downstream primer for cloning COVID19-S-C19 gene |

Note: The underline represents the digestion site.

1) The selected PCR primers and Colony PCR primers for amplifying COVID-19-S-C27 gene are shown in Table 3.

TABLE 3

| COVID-19-S-C27 gene amplification | | | | |
|---|---|---|---|---|
| Product No. | Product size | Primer No. | Primer sequence (5'-3') | Description |
| COVID19-S-C27 | 3741bp | COVID19-S-C27-Xho1-F1 | CCGCTCGAGATGTTCGTGTTTC TGGTG (SEQ ID NO: 12) | Upstream primer for cloning COVID19-S-C27 gene |
| | | COVID19-S-C27-Nhe1-R1 | CTAGCTAGCTTAGCCCTTCAGG CAGGAACAGCAG (SEQ ID NO: 13) | Downstream primer for cloning COVID19-S-C27 gene |

Note: The underline represents the digestion site.

2) The selected PCR primers and Colony PCR primers for amplifying COVID-19-S-C53 gene are shown in Table 4.

TABLE 4

| COVID-19-S-CS3 gene amplification | | | | |
|---|---|---|---|---|
| Product No. | Product size | Primer No. | Primer sequence (5'-3') | Description |
| COVID19-S-C53 | 3663bp | COVID19-S-C53-Xho1-F1 | CCGCTCGAGATGTTCGTGTTTC TGGTG (SEQ ID NO: 14) | Upstream primer for cloning COVID19-S-C53 gene |
| | | COVID19-S-C53-Nhe1-R1 | CTAGCTAGCTTAGAAGCCCAGC CAGATGTACC (SEQ ID NO: 15) | Downstream primer for cloning COVID19-S-C53 gene |

Note: The underline represents the digestion site.

3) The selected PCR primers and Colony PCR primers for amplifying COVID-19-S-C19HA gene are shown in Table 5.

TABLE 5

| | | COVID-19-S-C19 HA gene amplification | | |
|---|---|---|---|---|
| Product No. | Product size | Primer No. | Primer sequence (5'-3') | Description |
| COVID19-S-C19HA | 3792bp | COVID19-S-C19HA-XhoI-F1 | CCGCTCGAGATGTTCGTGTTTCT GGTG (SEQ ID NO: 16) | Upstream primer for cloning COVID19-S-C19HA gene |
| | | COVID19-S-C19HA-NheI-R1 | CTAGCTAGCTTAGGCATAATCTG GCACATCATAAGGGTAACAGCA GCTTCCACAAGAACAGCA (SEQ ID NO: 17) | Downstream primer for cloning COVID19-S-C19HA gene |

Note: The underline represents the digestion site.

4) The selected PCR primers and Colony PCR primers for amplifying SARS-COV-S-C19 gene are shown in Table 6.

TABLE 6

| | | SARS-COV-S-C19 gene amplification | | |
|---|---|---|---|---|
| Product No. | Product size | Primer No. | Primer sequence (5'-3') | Description |
| SARS-COV-S-C19 | 3711bp | SARS-COV-S-C19-XhoI-F1 | CCGCTCGAGATGTTCATCTTTCT GCTGTTC (SEQ ID NO: 18) | Upstream primer for cloning SARS-COV-S-C19 gene |
| | | SARS-COV-S-C19-NheI-R1 | CTAGCTAGCTTAACAGCAAGAT CCACAGGAGCA (SEQ ID NO: 19) | Downstream primer for cloning SARS-COV-S-C19 gene |

Note: The underline represents the digestion site.

5) The selected PCR primers and Colony PCR primers for amplifying MERS-CoV-S-C19 gene are shown in Table 7.

TABLE 7

| | | [MERS-COV-S-C19 gene amplification | | |
|---|---|---|---|---|
| Product No. | Product size | Primer No. | Primer sequence (5'-3') | Description |
| MERS-CoV-S-C19 | 3711bp | MERS-COV-S-C19-XhoI-F1 | CCGCTCGAGATGATACACTCAG TGTTTC (SEQ ID NO: 20) | Upstream primer for cloning MERS-CoV-S-C19 gene |
| | | MERS-COV-S-C19-NheI-R1 | CTAGCTAGCTTAATTACACTTAA GTTTTCCC (SEQ ID NO: 21) | Downstream primer for cloning MERS-CoV-S-C19 gene |

Note: The underline represents the digestion site.

6) Target gene acquisition: PCR amplification was performed by using pCDNA3.1 plasmid with the target gene sequence as a template and using primers in Table 4.

7) The digested product was purified according to the protocol of AxyPrep™ PCR Cleanup kit, and the concentration of the product was measured with Nano-300.

8) The purified product and vector were subject to double digestion (at 37° C. for 3 h).

9) Electrophoresis was performed with 1% Agarose gel; the corresponding DNA maker was used as a control to verify the PCR product; band on the gel was cut; the remaining PCR product was recovered; and the concentration of the product was measured with Nano-300.

10) The purified product was ligated into the vector (overnight at 16° C., ligation ratio: 1:5).

11) The ligation product was transformed according to the protocol of E. coli DB3.1 Competent Cells (TaKaRa).

12) The monoclonal clone on LB (Kana) plate was picked and added into a sterile 1.5 mL tube containing 200 µL LB (Kana) medium in advance, and incubated at 37° C. and 250 rpm for 3 h, and then Colony PCR was performed to screen positive clones.

13) After being identified by agarose gel electrophoresis, positive clones were selected and transferred to a 15 mL shake flask at a ratio of 1:500, and cultured at 37° C. and 250 rpm for 14-16 h.

14) The plasmid was extracted according to the protocol of the TIANGEN EndoFree Mini Plasmid Kit II.

15) The screened positive plasmid was identified by double digestion (XhoI and NheI, digested at 37° C. for 3 h).

16) After enzyme digestion and identification, the correct plasmid was selected for plasmid sequencing.

The constructed PCR products of different types of pseudoviruses are shown in FIG. 2. According to the experimental results, specific bands appeared at the corresponding of the six genes after PCR amplification, and molecular size of the bands was correct, indicating that the target bands were successfully amplified, and the sequencing results also indicated that the plasmid construction was successful.

Example 2 Infection of VSV-COVID-19-S-C19-HA on 293T-hACE2 Cells Showed Higher Efficiency To obtain VSV pseudoviruses of different truncated spike proteins (S) of COVID-19, plasmids pCAGGS-COVID-19-S, pCAGGS-COVID-19-S-C19, pCAGGS-COVID-19-S-C19-HA, pCAGGS-COVID-19-S-C27, and pCAGGS-COVID-19-S-C53 were transfected into 293T cells for packaging by liposomes (lipo2000), respectively. After 12 hours of transfection, dVSVΔG-Fluc-EGFP (prepared and stored in the laboratory), i.e., VSV replication-defective virus strain, was inoculated into culture medium corresponding to cells expressing COVID-19 intact spike protein or COVID-19-S-C19/C27/C53/C19-HA truncated protein, respectively (eukaryotic expression plasmids were transiently transferred 12 h in advance). Supernatant was collected, and anti-VSV-G neutralizing serum was added to block the infectivity of dVSVΔG-Fluc-EGFP remained in the supernatant. The progeny viruses were harvested to obtain pseudoviruses carrying the spike protein with different modifications of COVID-19 on the virus surface. Supernatants were collected 24 h, 48 h, and 72 h after dVSVΔG-FLuc-EGFP-GP infection, followed by centrifugation and filtration (0.45 μm pore size, Millipore) to remove cell debris, and long-term storage at −80° C. The number of EGFP-positive cells infected with 293T-hACE2 pseudovirus was counted by gradient dilution, and the titer of pseudovirus (unit: TU/ml) was measured and calculated.

Figures 3, 4:
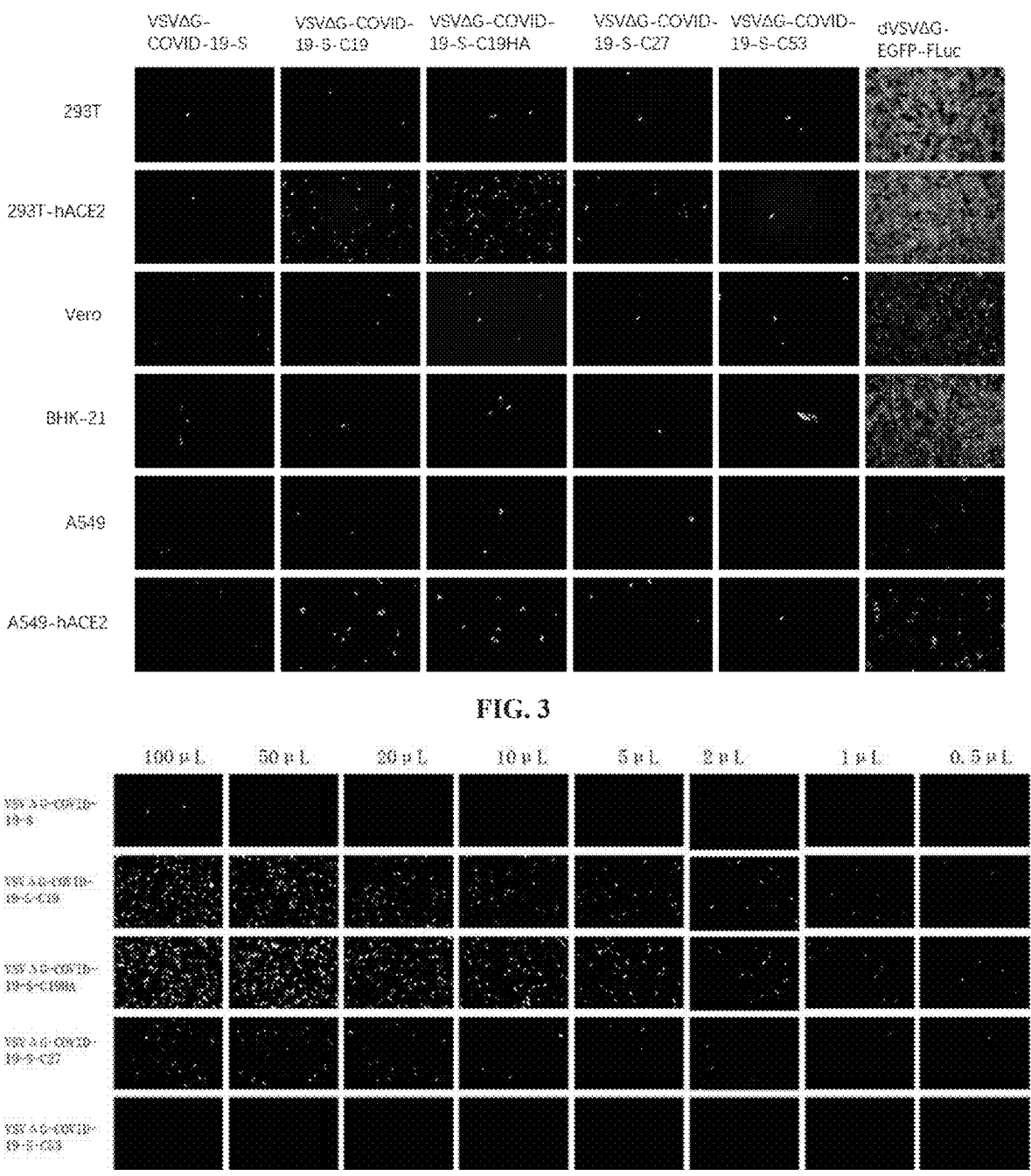
FIG. 3 shows comparison of infection efficiency of COVID-19 pseudoviruses packaged with different S-truncates in different cells.
FIG. 4 shows titer determination of different COVID-19 pseudoviruses in 293T-hACE2 detection cells.
Figure 5:
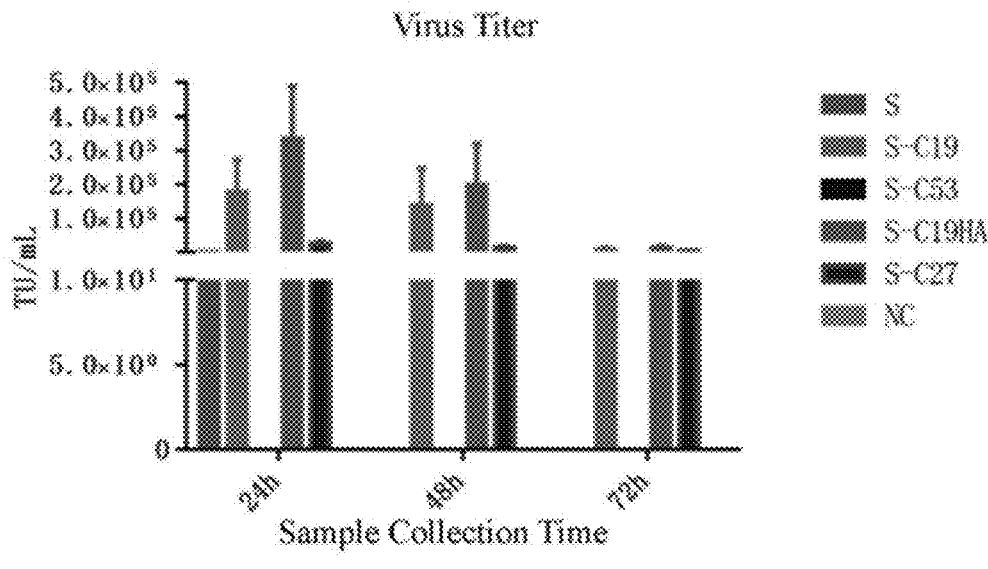
FIG. 5 shows effect of different sample collection time on titer of different types of pseudoviruses (different truncates at 3 end of S gene).

As shown in FIGS. 3 to 5, by comparing infection efficiency of VSV-mediated COVID-19 pseudoviruses, it is found that the pseudovirus packaged with full-length S had very low infection efficiency (EGFP and Fluc dual-reporter gene detection), indicating that the full-length S of COVID-19 is not suitable for packaging of COVID-19 pseudovirus. The truncated S-C19-HA pseudovirus had an infection efficiency about twice as high as that of S-C19. Although S-C19 could also package pseudovirus with higher titer, fusing a non-functional tag protein (other short peptides are also applicable) at 3 end of S-C19 can further improve the titer of the packaged COVID-19 pseudovirus, suggesting that the fused short peptide plays a role in stabilizing the spatial structure of coronavirus S. Further experiments showed that the packaging titer of MERS or SARS-S-C19HA was significantly higher than that of the control group (19 amino acids were deleted at C-terminal of S gene).

The sensitivity of 293T-hACE2 (stably and highly expressing hACE2) cells to COVID-19 pseudoviruses was further tested. First, 293 cells and BHK21 cells could hardly be infected by COVID-19 pseudoviruses (FIG. 3), and almost all of the cell lines stably expressing hACE2 receptor protein were infected by COVID-19 pseudovirus (each cell expressed green fluorescence under fluorescence microscope). Furthermore, in the above-mentioned one-step packaging system, the packaging titer of the obtained VSV-COVID-19-S-C19-HA (abbreviated as S-C19-HA) pseudovirus was about 4000 times of that of VSV-COVID-19-S full-length group. Similarly, the packaging titer of S-C19-HA was 15 times higher than that of VSV-COVID-19-S-C27 (abbreviated as S-C27) group. At the same time, the titer of COVID-19 pseudovirus decreased with the increase of collection times (at 24 h, 48 h, and 72 h, respectively). Particularly, the titer of the COVID-19 pseudovirus in the third collected supernatant (72 h) was low, which was mainly caused by poor cell status and change of pH value in the medium after long-term incubation (FIG. 4 and FIG. 5). The above problems could be solved by continuous perfusion culture technology.

Example 3 dVSVΔG-COVID-19-S-C19-HA Pseudovirus Packaged in 293T Cells had the Highest Titer The packaging efficiency of COVID-19 pseudoviruses is one of the major limiting factors for high-throughput detection of neutralizing antibody assay in vitro. In order to select the most suitable cell line for producing COVID-19 pseudoviruses, different cell lines were pre-plated in a 6-well cell culture plate, and common cells such as Vero-E6, BHK21, 293T-hACE2, and 293 were compared in this technology. Preferably, plasmids with different concentrations were transfected in the above different cell lines, and then dVSVΔG-COVID-19-S-C19-HA COVID-19 pseudovirus was packaged by referring to the following one-step packaging method. The specific steps are as follows:

1) plating Vero/BHK21/293T/293T-hACE2 cells in a 6-well plate, to have a suitable cell density of about 70% after 24 h;

2) diluting and uniformly mixing 0 μg, 0.25 μg, 0.5 μg, 1 μg, and 2 μg pCAGSGGGS-S/pCGGGS-S-C19/pCAGGS-S-C19-HA/pCAGGS-S-C27/pCAGGS-S-C53/pCAG GS-VSVG (positive envelope plasmid) in 100 μl opti-MEM, respectively, and diluting and uniformly mixing Lipofectamine LTX in 100 μl opti-MEM (plasmid:transfection reagent=1:3);

3) slowly mixing the plasmid diluent with the Lipofectamine LTX diluent, and then standing at room temperature for 20 min;

4) replacing the complete medium with opti-MEM, adding the mixed solution into the culture medium, gently mixing, culturing at 37° C. with 5% $CO_2$ for 6 h, and then replacing the opti-MEM with complete medium;

5) adding dVSVΔG-Fluc-EGFP virus to infect the cells with MOI=1 after cell culture for 12 h;

6) collecting virus supernatant 24 h, 48 h and 72 h after virus infection, respectively, adding 1 μl anti-VSVG serum per 1 mL virus suspension, and incubating in a cell incubator for 2 h;

7) infecting 293T-hACE2 cells after gradient dilution, calculating the number of EGFP positive cells after pseudovirus infection, and measuring and calculating the titer of the pseudovirus (unit: TU/ml);

8) observing EGFP fluorescence expression 48 h after virus infection; and 9) determining the optimal cell type for packaging according to the packaging titer of the pseudovirus.

Figure 6:
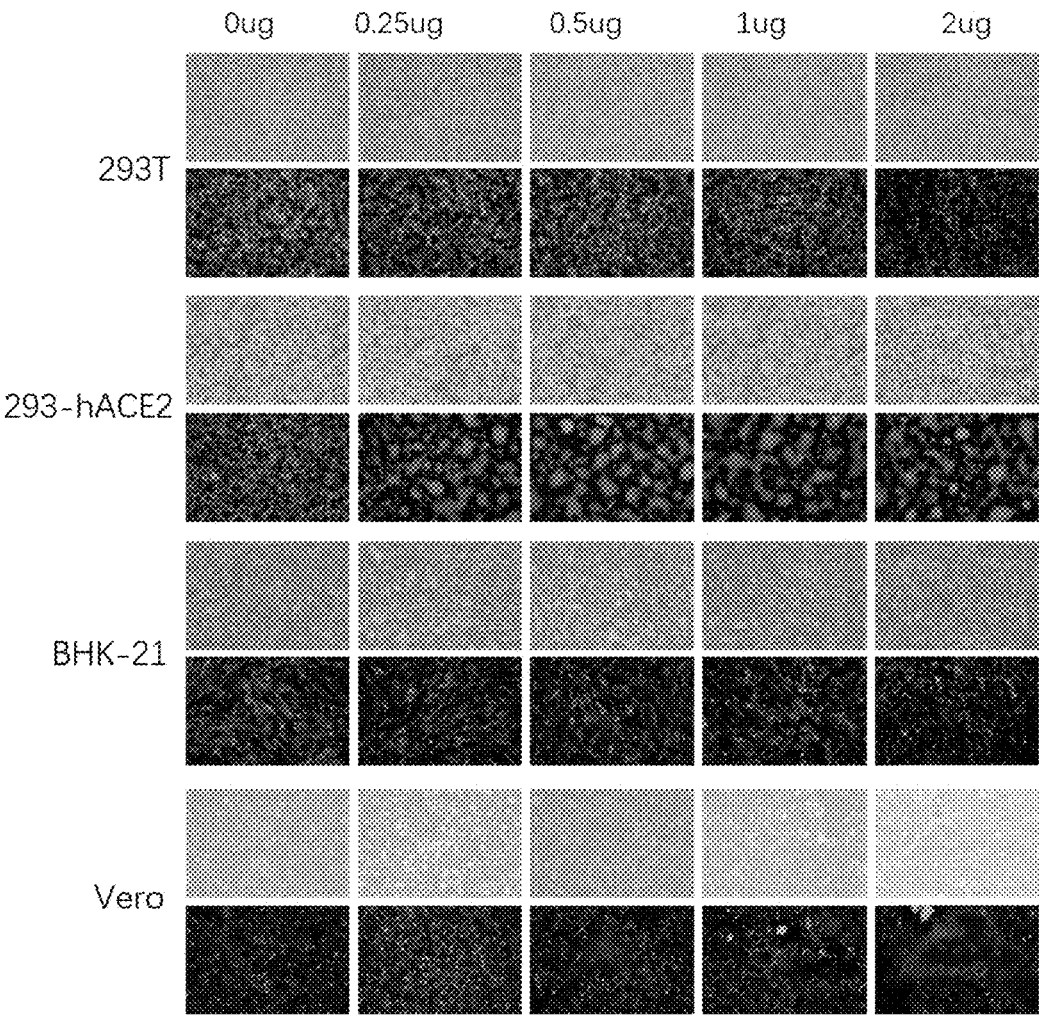
FIG. 6 shows effect of pre-transfection with different amounts of envelope plasmid (pCA-C19-NA) on pseudovirus titer.
Figure 7:
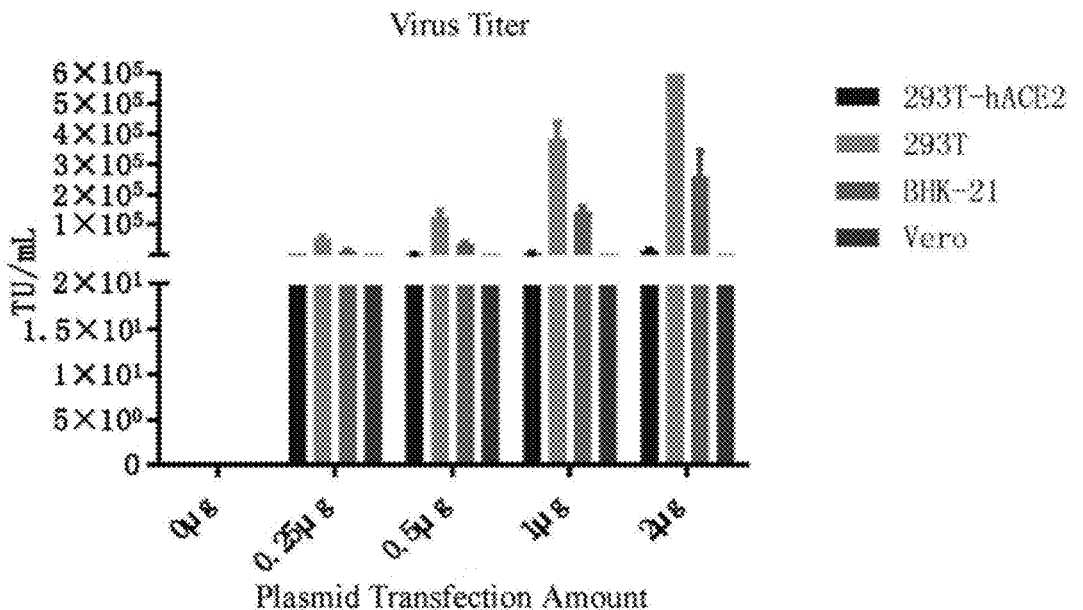
FIG. 7 shows effect of transfection amount of spike protein in different packaging cells on titer of packaging COVID-19 pseudovirus.

The statistical results showed that 293T-hACE2 produced strong cell fusion during the packaging process (FIG. 6), while it was relatively rare for other cells. The virus titer gradually increased with increase of the amount of plasmid for transfection, and the highest titer of packaged pseudovirus was obtained when 2 μg plasmid was transfected. However, the high concentration of plasmid also affected the state of cells (excessive S protein aggregation caused certain toxicity to cells). The standard TCID50 (Karber method) statistics showed that the dVSVΔG-COVID-19-S-C19-HA pseudovirus had the highest titer (FIG. 7). It was also found that the supernatant of the package collected at 24 h contained about 5E5 effective virus particles per milliliter.

Example 4 Effect of Initial Inoculation Amount (MOI) of VSV Replication-Defective Virus on COVID-19 Pseudovirus Yield in One-Step Pseudovirus Packaging Method In order to further improve the packaging system to obtain higher packaging titer of pseudovirus, the initial inoculation amount of VSV replication-defective virus (dVSVΔG-Fluc-EGFP) was further tested. First, 293T packaging cells (stably expressing COVID-S-C19-HA protein) were infected according to different MOIs. The virus solution was collected 24 h after infection, and the virus titer was determined. The specific steps are as follows:

1) plating 293T cells in a 6-well plate, to have an optimal cell density of about 70% after 24 h;
2) diluting and uniformly mixing 1 μg pCAGGS-S-C19-HA plasmid in 100 μl opti-MEM, and diluting and uniformly mixing Lipofectamine LTX in 100 μl opti-MEM (plasmid:transfection reagent:=1:3);
3) slowly mixing the plasmid diluent with the Lipofectamine LTX diluent, and then standing at room temperature for 20 min;
4) replacing the complete medium with opti-MEM, adding the mixed solution into the culture medium, gently mixing, culturing at 37° C. with 5% $CO_2$ for 6 h, and then replacing the opti-MEM with complete medium;
5) adding dVSVΔG-Fluc-EGFP virus to infect the cells with MOI=0, 0.01, 0.1, 0.5, 1, 2, 5 after cell culture for 12 h;
6) collecting virus supernatant 24 h after virus infection, adding 1 μL anti-VSVG serum per 1 mL virus solution, and incubating in a cell incubator for 2 h;
7) infecting 293T-hACE2 cells after gradient dilution, calculating the number of EGFP-positive cells after pseudovirus infection, and measuring and calculating the titer (unit: TU/mL) of the pseudovirus;
8) observing EGFP fluorescence expression 48 h after virus infection; and
9) determining the optimal cell type for packaging according to the packaging titer of the pseudovirus.

Figure 8:
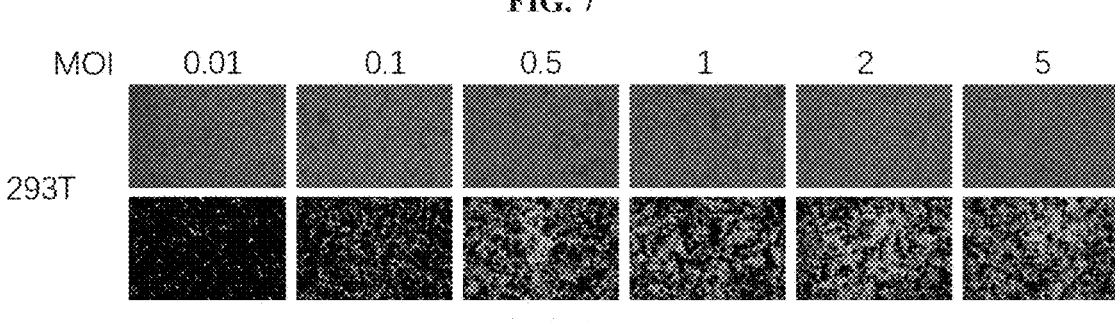
FIG. 8 shows expression of fluorescent reporter gene in 293T cells infected with dVSVΔG-Fluc-EGFP with different MOIs.
Figure 9:
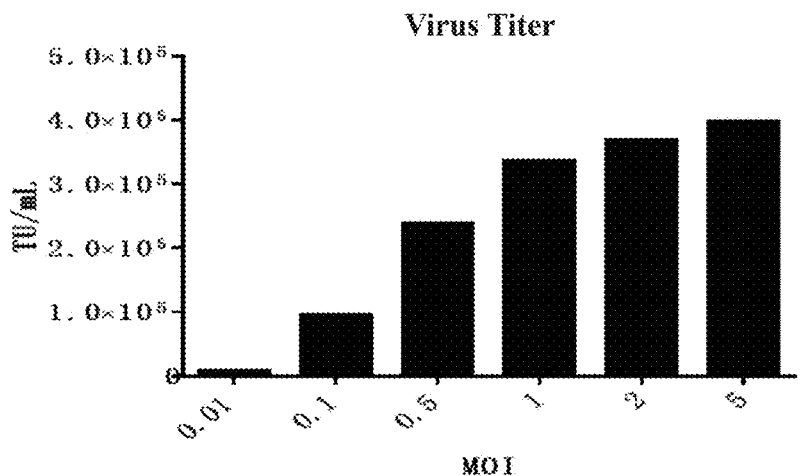
FIG. 9 shows effect of adding VSV replication-defective virus with different MOIs to 293T cells on efficiency of assembling COVID-19 pseudovirus.

The results showed that with increase of the MOI value of the added dVSVΔG-Fluc-EGFP replication-defective virus, the cell infection was gradually enhanced (FIG. 8), and the titer of the harvested COVID-19 pseudovirus was gradually increased. When the initial MOI=1, the titer of the packaged COVID-19 pseudovirus gradually entered a plateau (FIG. 9). Therefore, the initial multiplicity of infection (MOI) can be controlled in the range of 0.1 to 5, and the optimal MOI is MOI=1.

Example 5 Effect of Pre-Transfection Time of Coronavirus Envelope Expression Plasmid on Titer of Packaged Pseudovirus In the coronavirus pseudovirus packaging system, pre-transfection time of coronavirus envelope plasmid is another factor affecting pseudovirus titer. The effect of pre-transfection time of envelope eukaryotic expression plasmid on pseudovirus titer was further tested. First, dVSVΔG-Fluc-EGFP replication-defective virus was infected with MOI=1, 12 h and 24 h after plasmid transfection, the virus suspension was collected 24 h later, and the titer of the packaged pseudovirus was measured. The specific steps are as follows:

1) plating 293T cells in a 6-well plate, to have an optimal cell density of about 70% after 24 h;
2) diluting and uniformly mixing 1 μg pCAGGS-S-C19-HA plasmid in 100 μl opti-MEM, and diluting and uniformly mixing Lipofectamine LTX in 100 μl opti-MEM (plasmid:transfection reagent=1:3);
3) slowly mixing the plasmid diluent with the Lipofectamine LTX diluent, and then standing at room temperature for 20 min;
4) replacing the complete medium with opti-MEM, adding the mixed solution into the culture medium, gently mixing, culturing at 37° C. with 5% $CO_2$ for 6 h, and then replacing the opti-MEM with complete medium;
5) adding dVSVΔG-Fluc-EGFP virus to infect the cells with the optimal MOI=1 after cell culture for 12 h and 24 h, respectively;
6) collecting virus supernatant 24 h after virus infection, adding 1 μL anti-VSVG serum per 1 mL virus solution, and incubating in a cell incubator for 2 h;
7) infecting 293T-hACE2 cells after gradient dilution, calculating the number of EGFP-positive cells after pseudovirus infection, and measuring and calculating the titer of COVID-19 pseudovirus (unit: TU/mL); and
8) observing EGFP fluorescence expression 48 h after virus infection.

Figure 10:
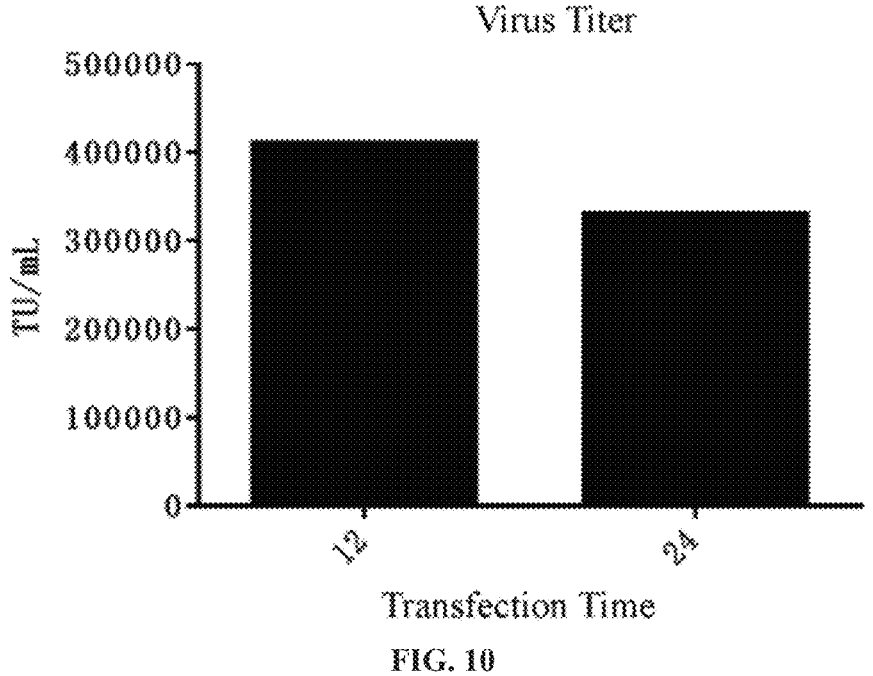
FIG. 10 shows effect of different transfection time of COVID-19 envelope plasmid (pCA-COVID-19-C19 HA) on packaging efficiency.

The results showed that when the envelope plasmid was pre-transfected for 12 h, the pseudovirus titer was slightly higher than that when the plasmid was transfected for 24 h (FIG. 10). With the increase of pre-transfection time, it was found that the state of cells was poor at the time of virus collection, and the pH change of the culture medium affected virus production of the cells. Therefore, the optimal pre-transfection time was 12 h. Meanwhile, the optimal pre-transfection time of the transient expression system was around 12 h. When TetOn was used to induce expression of coronavirus S protein, an inducer should be added 12 h in advance to induce stable expression of envelope protein in cells, and then VSV replication-defective virus was added for packaging of coronavirus pseudovirus.

Example 6 Comparison of Inducible System and Plasmid Transient Transfection Packaging, and Exploration of Different Concentrations of Dox in Inducible System Packaging In the coronavirus pseudovirus packaging system, packaging cells transiently or stably or inductively expressed the coronavirus spike protein, wherein the transient expression was realized by transfecting the cells with eukaryotic expression vector; the stable expression was realized by transducing cells with a lentiviral vector system; and the inducible expression was achieved by transducing cells with a tetracycline-regulated tet-on/off vector system.

The pseudovirus packaging process of the inducible system is as follows:

1) plating 293T-19HA cells 40 h in advance (the plate can be a 6-well plate, T75 bottle, T175 bottle, cell factory, or the like, which can be selected according to actual needs);
2) replacing culture medium for the plated cells with complete medium containing 500 ng/ml DOX 24 h in advance, and culturing at 37° C. with 5% $CO_2$;
3) adding VSV envelope pseudoviruis with MOI=0.5-5; and
4) harvesting the first, second, and third supernatants at 24 h, 48 h, and 72 h, respectively centrifuging the supernatants at 2000 g after each harvesting, taking the supernatants after 10 min, and storing them at 4° C.

When TetOn was used to induce expression of coronavirus S protein, an inducer should be added 12 h in advance to induce stable expression of envelope protein in cells, and then VSV replication-defective virus was added for packaging of coronavirus pseudovirus. In this example, the results of the inducible system and the plasmid transient transfection packaging were compared.

The packaging process of plasmid transient transfection is as follows:

1) plating 293T cells 24 h in advance (the plate can be a 6-well plate, T75 bottle, T175 bottle, cell factory or the like, which can be selected according to actual needs);

2) replacing culture medium for the plated cells with serum-free medium 8 h in advance, then performing plasmid transfection by mixing the transfection reagent PEI with plasmid pcDNA-19HA to be transfected in 3:1, incubating them at room temperature for 15 min, and then adding them to the cell culture medium that has been replaced with serum-free medium;

3) adding VSV envelope pseudovirus with MOI=0.5-5; and 4) harvesting the first, second, and third supernatants at 24 h, 48 h, and 72 b, respectively centrifuging the supernatants at 2000 g after each harvesting, taking the supernatants after 10 min, and storing them at 4° C.

Figure 11:
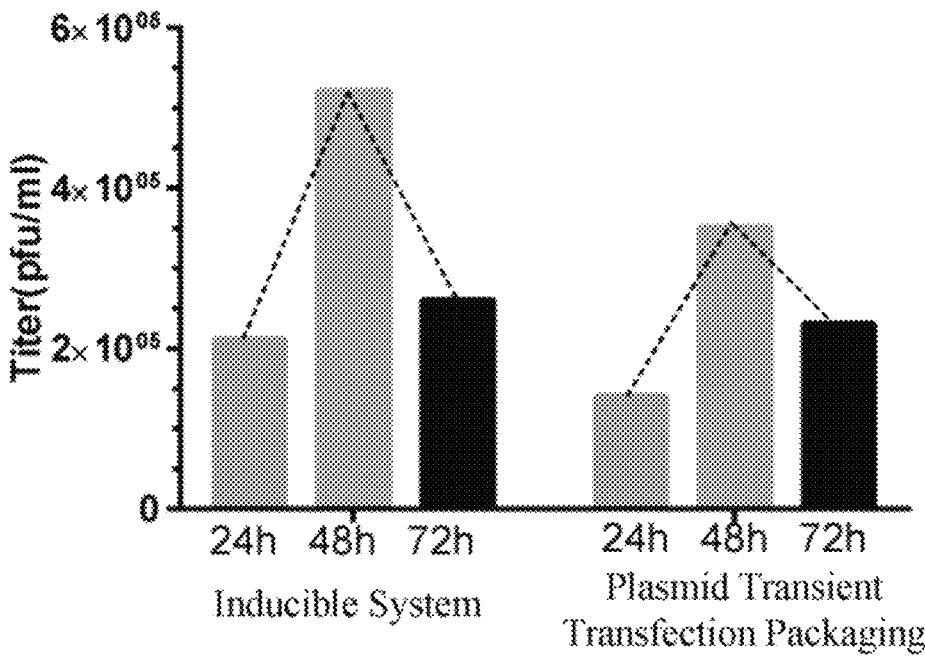
FIG. 11 shows effect of plasmid transient expression and inducible expression system and pseudovirus packaging sample collection time on titer of packaged pseudovirus.

It can be seen from the results shown in FIG. 11 that the titers of the supernatants harvested at 24 h, 48 h, and 72 h in the inducible system packaging were better than those in the plasmid transient transfection packaging. In the figure, the X-axis shows the supernatant samples collected at 24 h, 48 h, and 72 h after the inducible system and the plasmid transient transfection packaging, and the Y-axis shows the virus titer (pfu/ml) after the TCID50 detection of the supernatants. Meanwhile, the supernatants harvested at 24 h, 48 h, and 72 h were stored at 4° C. after harvesting, and the titer was detected at the same time.

By applying the above steps, this example also studied the effect of different DOX concentrations in the inducible system on the titer of the packaged pseudovirus.

Figures 12, 13:
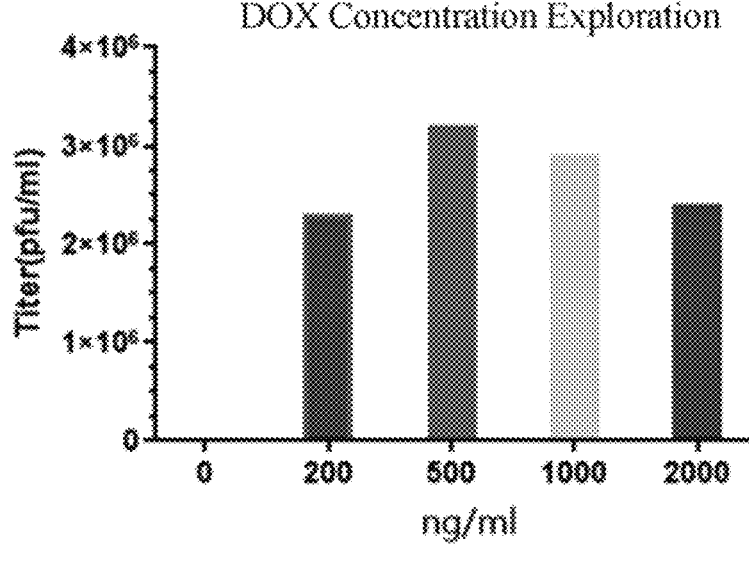
FIG. 12 shows effect of different DOX concentrations in the inducible packaging system on titer of packaged pseudovirus.
FIG. 13 shows determination of package titer of different types of coronavirus at different temperatures.

The results are shown in FIG. 12. The X-axis shows the concentrations of DOX in the packaging with the inducible system, 0 ng/ml, 200 ng/ml, 500 ng/ml, 1000 ng/ml, and 2000 ng/ml, and the Y-axis shows the virus titer (pfu/ml) after TCID50 detection of the supernatants. The harvesting virus was performed at 48 h. It can be seen from FIG. 12 that the titer of COVID-19 pseudovirus packaged with DOX at 500 ng/ml was the highest.

Example 7 Effect of Culture Temperature on Virus Producing Titer of Pseudoviruses with Different Modified Envelopes The temperature during virus packaging can affect the state of cells as well as the pH change of culture medium, and further has a great impact on the stability of some viruses. Therefore, the key factor of pseudovirus packaging, that is, culture temperature of packaging cells, was further detected. The specific steps are as follows:

1) plating 293T cells in a 6-well plate, to have an optimal cell density of about 70% after 24 h;

2) diluting and uniformly mixing 1 µg plasmids pCAGGS-COVID-19-C19-HA, pCAGGS-SARS-CoV-C19, pCAGGS-MERS-CoV-C19, and VSVG in 100 µl opti-MEM, and diluting and uniformly mixing Lipofectamine LTX in 100 µl opti-MEM (plasmid: transfection reagent=1:3);

3) slowly mixing the plasmid diluent with the Lipofectamine LTX diluent, and then standing at room temperature for 20 min;

4) replacing the complete medium with opti-MEM, adding the mixed solution into the culture medium, gently mixing, culturing at 37° C. with 5% $CO_2$ for 6 h, and then replacing the opti-MEM with complete medium;

5) adding dVSVΔG-Fluc-EGFP virus to infect the cells with MOI=0.5 after cell culture for 12 h;

6) culturing the infected cells in incubators at 37° C., 35° C., and 32° C., respectively, for 24 h, collecting virus supernatants, adding 1 µL anti-VSVG serum per 1 mL virus solution, and incubating in a cell incubator for 2 h;

7) infecting 293T-hACE2 cells after gradient dilution, calculating the number of EGFP-positive cells after pseudovirus infection, and measuring and calculating the titer (unit: TU/ML) of the pseudovirus; and 8) observing EGFP fluorescence expression 48 hr after virus infection.

The results showed that the temperature could greatly affect virus titer for COVID-19 pseudoviruses, and the virus titer gradually increased with decrease of temperature. When packaging COVID-19 pseudoviruses, the optimal temperature for culturing packaging cells was 32° C., while for SARS, MERS, and VSV replication-defective pseudoviruses, ideal viral load could be obtained at 35° C.; (FIG. 13).

Example 8 Stability Test of COVID-19 Pseudoviruses with Different Envelope Modifications It is known that the titer and stability of a stock solution of packaged pseudovirus are important factors affecting the long-term storage and viral load of the virus. The titer and storage stability of COVID-19 pseudovirus packaged based on VSV replication-defective vector and COVID-19 pseudovirus packaged based on RV (retroviral vector system) system were compared in parallel. The specific steps are as follows:

1) plating 293T cells in a 6-well plate, to have an optimal cell density of about 70% after 24 h;

2) diluting and uniformly mixing 1 µg pCAGGS-COVID-19-C19-HA plasmid in 100 µl opti-MEM, and diluting and uniformly mixing Lipofectamine LTX in 100 µl opti-MEM (plasmid:transfection reagent=1:3); diluting and uniformly mixing 1 µg pCAGGS-COVID-19-C9-HA, 1.5 µg pcgp, 2 µg pRV in 100 µl Opti-MEM, and diluting and uniformly mixing Lipofectamine LTX in 100 µl Opti-MEM (plasmid:transfection reagent=1:3);

3) slowly mixing the plasmid diluent with the Lipofectamine LTX diluent, and then standing at room temperature for 20 min;

4) replacing the complete medium with opti-MEM, adding the mixed solution into the culture medium, gently mixing, culturing at 37° C. with 5% $CO_2$ for 6 h, and then replacing the opti-MEM with complete medium;

5) for VSV pseudovirus, adding dVSVΔG-Fluc-EGFP virus to infect the cells with MOI=0.5 after cell culture for 12 h;

6) for VSV pseudovirus, culturing the infected cells in an incubator at 37° C. for 24 h, collecting virus supernatant, adding 1 anti-VSV VG serum per 1 mL virus solution, and incubating in the cell incubator for 2 h; and 7) subjecting VSV-packaged COVID-19 pseudovirus to repeated freezing-thawing for 0, 1, 2, and 3 cycles, storing the virus stock solution at 4° C., −20° C., and −80° C. for 3 d and 7 d, infecting 293T-hACE2 cells after gradient dilution, and calculating the number of EGFP-positive cells after pseudovirus infection (VSV pseudovirus system); for COVID-19 pseudovirus packaged with pRV, collecting samples 36 h after infection, and storing them at 4° C. and −80° C. for different times, and then calculating the virus titer according to TCID50 (Karber method).

Figure 14:
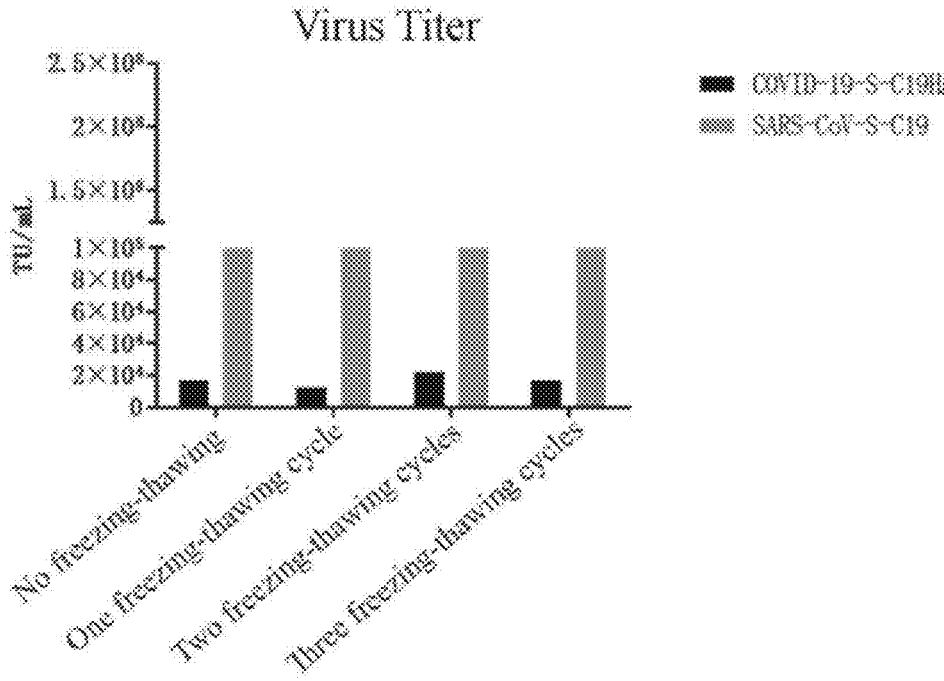
FIG. 14 shows stability test of different coronavirus pseudoviruses mediated by VSV vector, and effect of different temperatures on stability of coronavirus pseudoviruses.
Figure 15:
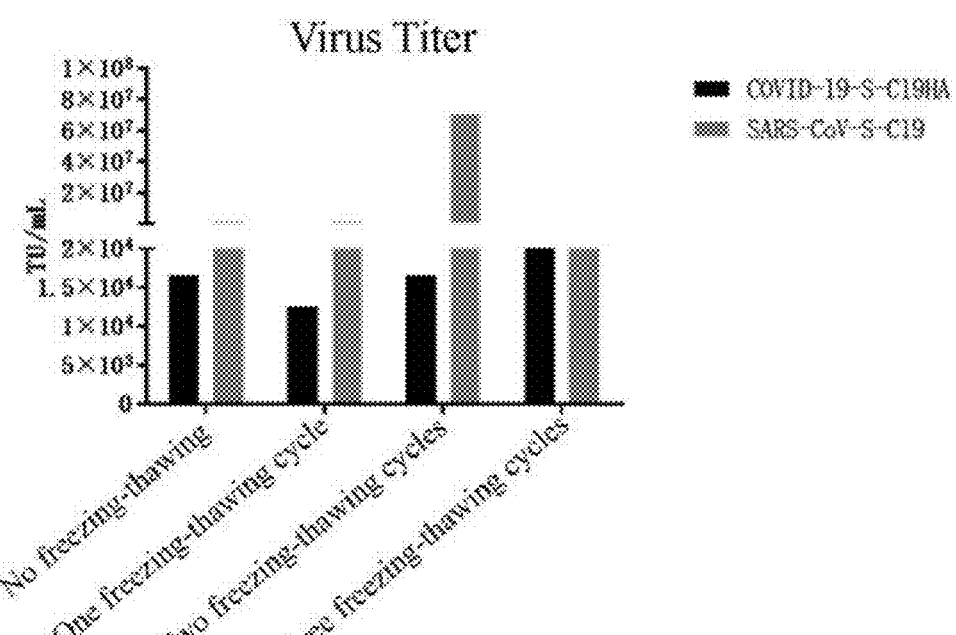
FIG. 15 shows stability test of different coronavirus pseudoviruses mediated by VSV vector, and effect of repeated freezing-thawing on stability of coronavirus pseudoviruses.
Figure 16:
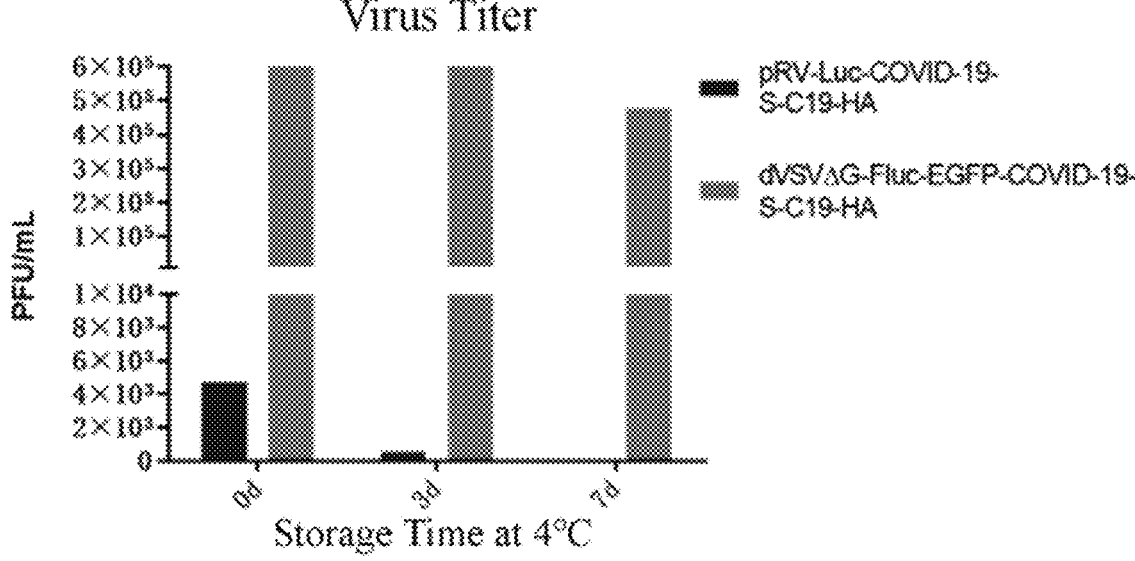
FIG. 16 shows effect of storage time at 4° C. of COVID-19 pseudovirus system mediated by dVSVΔG-Fluc-EGFP dual-reporter genes vs. COVID-19 pseudovirus system mediated by pRV-Fluc (retroviral vector) on stability of pseudovirus.

The results showed that, as shown in FIG. 14 to FIG. 16, the virus titers of the two pseudoviruses changed little after three freezing-thawing cycles, the titers of COVID-19 stored at 4° C., −20° C., and −80° C. had little effect on the titers on the 7th day, and COVID-19 mediated by the pRV system had low titer and short storage time, so it was not suitable for large-scale detection. In addition, low initial virus titer will affect stability of the virus in long-term storage. The initial titer of dVSVΔG-COVID-19-S-C19-HA pseudovirus packaged by one-step method based on VSV system was 6E5 pfu/ml, which was nearly 100 times higher than that of pRV system, and the titer remained stable at 4° C. for 7 days.

Example 9 Pseudovirus-Based Neutralizing Antibody Detection 293T-hACE2 cells were inoculated in a 96-well plate in advance. Mouse serum was collected by orbital vein blood sampling, diluted with DMEM complete medium, and then diluted according to a 2-fold gradient, mixed with dVSV-COVID-19-S-C19-HA virus (6000TU), dVSV-SARS-CoV-S-C19 (500TU), and dVSS-MERS-CoV-S-C19 (500TU) respectively, and incubated at 37° C. for 2 h. The mixture of virus and antibody was resuspended in 10% FBS-DMEM, and the mixture was added to 293T-hACE2 cell suspension to be detected. After 48 h of culture, a green fluorescence image was taken with fluorescent photography equipment (Nikon microscope). For quantitative detection, cold fluorescence readout of Fluc reporter gene was determined, and neutralization titer of the antibody was calculated.

In order to verify whether the pseudoviruses prepared by packaging can be used to detect antibody neutralization activity through neutralization assay, the prepared antisera of COVID-19, SARS-CoV, and MERS-CoV were used for pseudovirus neutralization assay. The specific steps are as follows:

1) plating 293T-hACE2 cells on a 96-well plate, to have a cell density of about 70% after 24 h;
2) diluting serum in gradient, mixing it with pseudovirus of the same volume, setting a duplicate well, and setting a pseudovirus control which was not mixed with the serum and a blank cell control which was only added with a culture medium;
3) placing in an incubator at 37° C. with 5% $CO_2$ for 2 h;
4) inoculating the serum-pseudovirus mixture in the previous step into a 96-well plate, and culturing at 37° C. with 5% $CO_2$ for 48 h; and
5) photographing, calculating and detecting the activity of firefly luciferase (FLuc).

Figure 17:
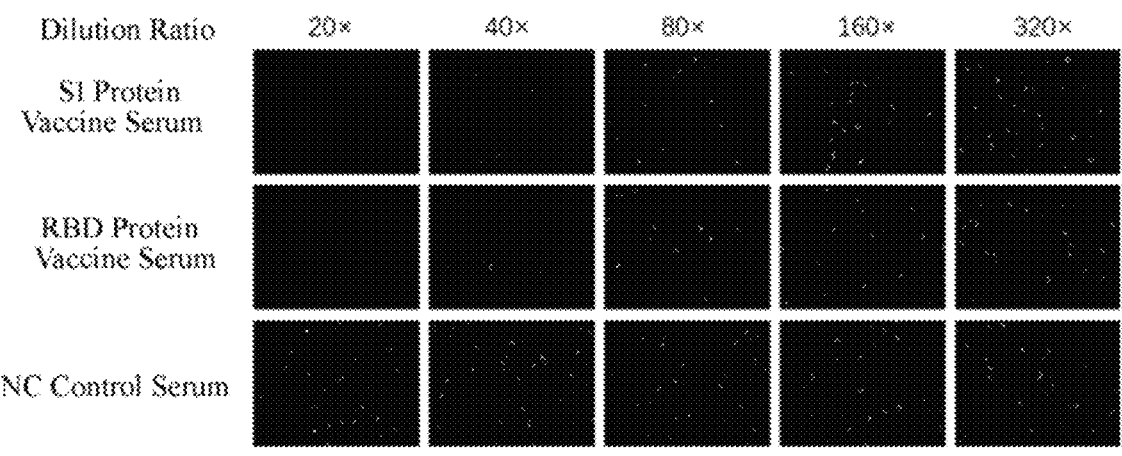
FIG. 17 shows neutralizing antibody titer detection (IC90) against COVID-19 pseudovirus, and 293T-hACE2 cell infection-pseudovirus neutralizing antibody detection.
Figure 18:
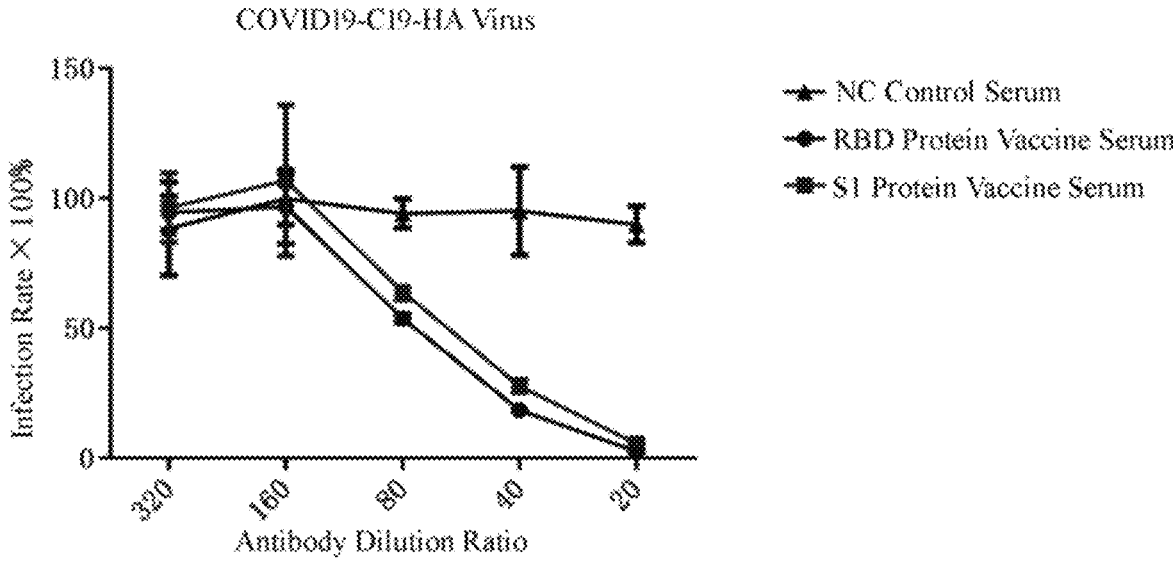
FIG. 18 shows neutralizing antibody titer detection (IC90) against COVID-19 pseudovirus, and pseudovirus neutralizing antibody—Fluc enzyme activity detection.
Figure 19:
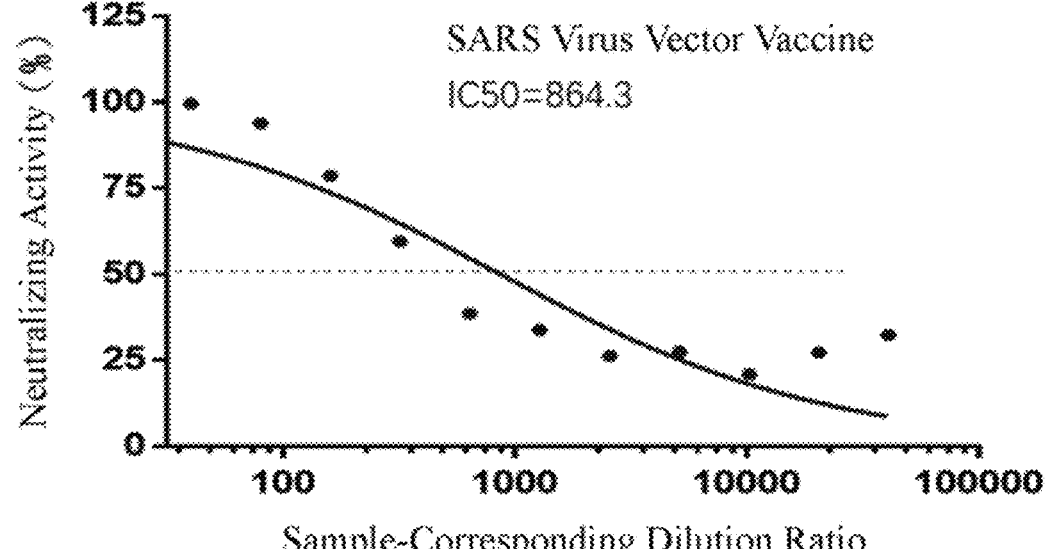
FIG. 19 shows detection of neutralizing antibody against SARS virus vector vaccine.

It can be seen from the results (as shown in FIG. 17 to FIG. 19) that the pseudovirus packaging SARS involved in this disclosure was used to detect antibodies with virus neutralizing efficacy produced by different types of vaccines.

It can be seen from FIG. 18 that the serum IC50 of S1 protein vaccine was 56.9; and the IC50 of RBD protein vaccine was 68.35 (defined as a serum sample diluted 68.35 times that can effectively organize the infection of E3 virions). The COVID-19 pseudovirus system used COVID-19-S-C19-HA. The background value of the control group was very low, and the stability of different dilutions was high. In this example, the design route refers to the method shown in FIG. 1, dVSVΔG-Fluc-EGFP one-step method for packaging pseudovirus was used to continuously develop SARS-CoV pseudovirus. As shown in FIG. 19, the activity of neutralizing antibody produced by the candidate vaccine was detected by using the SARS pseudovirus packaged by the above operation technology, and the IC50 in the serum of mice immunized with SARS virus vector vaccine was about 864.3 (FIG. 19). In this technical solution, dVSVΔG-Fluc-EGFP-SARS-C19 was used for SARS pseudovirus, and 293T-hACE2 cells were used to detect the activity of neutralizing antibody, which was consistent with the method for detecting neutralizing antibody of COVID-19. Meanwhile, further analysis showed that the serum immunized with SARS vaccine had no obvious cross reaction with COVID-19 pseudovirus, the SARS pseudovirus in this example showed an excellent confidence interval, and the background Fluc value obtained from the control serum detection tended to be a parallel line, indicating that the stability and repeatability of the pseudovirus in neutralizing antibody activity detection is consistent with the conclusion of VSV mediated COVID-19 pseudovirus. The pseudovirus developed based on the dVSVΔG-Fluc-EGFP packaging system maintained a high biological titer (the titer of SARS pseudovirus was 8E6 pfu/ml), which was significantly higher than that of COVID-19 pseudovirus, and its stability was consistent with that of other coronavirus pseudoviruses. It is further concluded that the dVSVΔG-Fluc-EGFP packaging system can be adapted for the development of other known coronavirus pseudoviruses.

In the following two examples, coronavirus pseudovirus was used as a biological indicator to evaluate the efficacy of a virucidal disinfectant:

Example 10 Use of Pseudoviruses of COVID-19 and its Variants to Examine and Evaluate Disinfecting Ability of Ozone (1) Preparation of biological indicator of COVID-19 pseudovirus reporting system
a. adding dVSVΔG-Fluc-EGFP to 293T cells stably expressing VSV envelope protein GP, collecting the supernatant 24 h later to obtain the amplified VSV replication-defective virus, and determining the titer thereof;
b. passaging the packaging cells 293T expressing COVID-19 Spike protein (S protein) into 60 mm dish, transfecting with eukaryotic expression plasmid by LipoLTX liposome, adding dVSVΔG-Fluc-EGFP after 12 h of transfection (the multiplicity of infection (MOI) was 0.1 to 5), culturing in an incubator at 32° C. to 37° C., harvesting the pseudovirus supernatant after 24 h, then treating with anti-VSV neutralizing antibody for 2 h, and filtering with a 0.22 um filter membrane to obtain the COVID-19 pseudovirus.

(2) Construction of virus-contaminated environment
A refrigerator was adopted to simulate an environmental temperature of low-temperature cold chain transportation of −40° C. to −20° C., 50 µl COVID-19 pseudovirus with an initial titer of 2*10⁶ TU/ml obtained by packaging was diluted and evenly smeared on six 6 cm plastic culture dishes, 50 μl COVID-19 pseudovirus was added to each dish with an initial titer of $2*10^6$ TU/ml.

(3) Ozone was introduced into the experimental refrigerator at −40° C. to −20° C. for 30 min. When the detected ozone concentration was stable at 1-50 ppm, three 6 cm culture dishes were put in as the experimental group, and the other three 6 cm culture dishes were put into the control refrigerator at the same temperature without ozone.

(4) At three different times, 10 min, 30 min, and 60 min, a 6 cm culture dish was taken from the experimental refrigerator and the control refrigerator respectively for titer test:

1) diluting the virus in dish with a dilution gradient of $10^{-1}$ to $10^{-6}$ into a 96-well plate;

2) plating 293T-ACE2 cells in the 96-well plate with 20000 cells, 100 μl, per well and mixing with the diluted virus;

3) culturing at 37° C. with 5% $CO_2$ for 24 h, photographing with fluorescent photography equipment, calculating and detecting the activity of firefly luciferase (FLuc), and calculating the titer.

Figure 20:
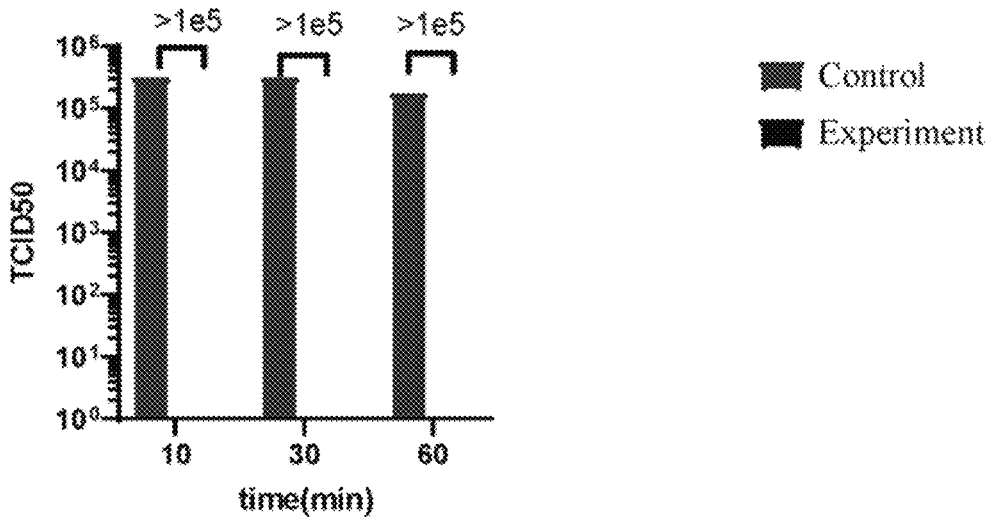
FIG. 20 is a graph showing activity change of COVID-19 killed by ozone at room temperature.
Figure 21:
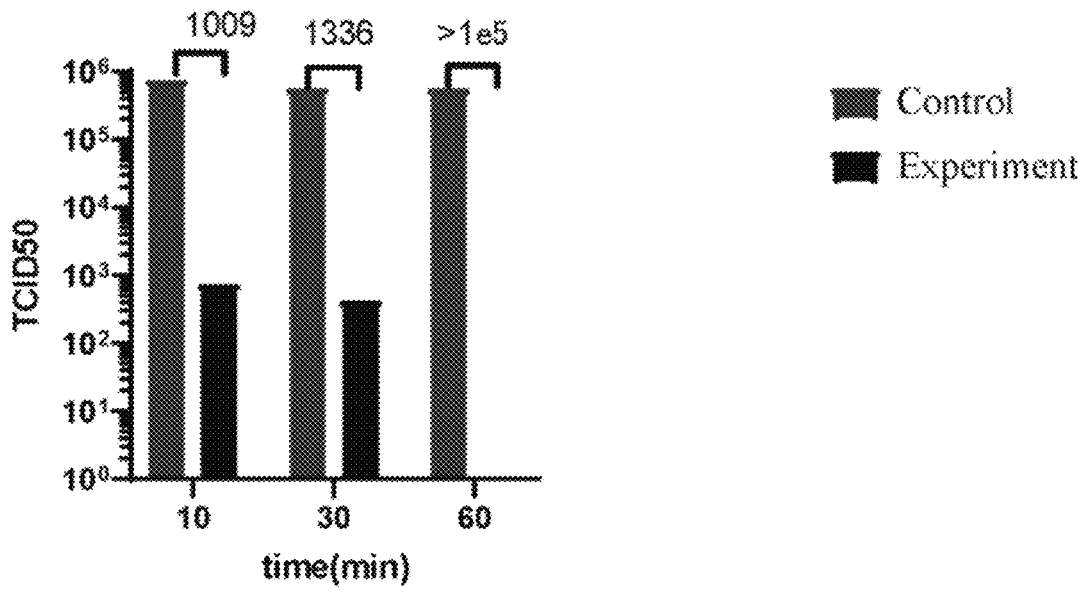
FIG. 21 is a graph showing activity change of COVID-19 killed by ozone at −20° C.

According to the results (as shown in FIG. 20-21), when the ozone concentration is maintained at 1-200 ppm and the temperature is set at low temperature (−40° C. to −20° C.) and room temperature, ozone has a good ability to disinfect COVID-19 pseudoviruses. As the ozone inactivation time increases, the disinfection will continue to work, and the virus titer will be significantly reduced. According to the analysis of the influence of temperature, the higher the ambient temperature during disinfection, the stronger the ability of ozone to disinfect COVID-19, and COVID-19 pseudovirus can be almost completely inactivated after 10 min of disinfection at room temperature. For the simulated low-temperature cold chain environment at a temperature of −20° C., the experimental results show that the instantaneous disinfecting rate of ozone on COVID-19 pseudovirus in this environment is considerably high. The longer the time, the better the disinfecting effect, and the titers are all in a lower state. After a certain period of time, ozone can also achieve complete inactivation of the virus, showing better disinfecting ability.

---

What is claimed is:

1. A coronavirus pseudovirus packaging system, comprising a modified vesicular stomatitis virus (VSV) and a packaging cell that expresses a coronavirus spike protein; wherein the coronavirus is SARS, MERS, or COVID-19 virus, and the amino acid sequence of the spike protein is set forth in SEQ ID NO: 4 or SEQ ID NO: 5 or SEQ ID NO: 6 or SEQ ID NO: 7; the modified vesicular stomatitis virus VSV is defined as a replication-defective virus with structural gene replaced by Fluc and EGFP dual-reporter genes, the modified vesicular stomatitis virus VSV is named as dVSVΔG-Fluc-EGFP, a gene coding GP in the genetic material of the VSV is replaced by Fluc reporter gene, the EGFP reporter gene is integrated between Fluc and VSV polymerase L gene, and the gene sequence of the dVSVΔG-Fluc-EGFP is set forth in SEQ ID NO: 3.

2. The coronavirus pseudovirus packaging system according to claim 1, wherein the packaging cell is selected from 293, 293T, 293sus, HEK293, HEK293T, HEK293FT, BHK, or Vero, and the packaging cell transiently or stably or inductively expresses the coronavirus spike protein, the transient expression is realized by transfecting the cell with an eukaryotic expression vector, the stable expression is realized by transducing the cell with a lentiviral vector system, and the induced expression is realized by transducing the cell with a tetracycline-regulated tet-on/off vector system.

3. A one-step packaging method for a pseudovirus packaging system, wherein the pseudovirus packaging system comprises the coronavirus pseudovirus packaging system according to claim 1, expression of the coronavirus spike protein is mediated by a transient expression plasmid or a stable expression plasmid or a stable and inducible expression lentivirus vector, dVSVΔG-Fluc-EGFP and the packaging cell that expresses the coronavirus spike protein are mixed in one step, and supernatant is collected after a certain time to obtain the coronavirus pseudovirus.

4. The one-step packaging method for the pseudovirus packaging system according to claim 3, comprising the following steps:

(1) adding dVSVΔG-Fluc-EGFP to 293T cell that transiently or stably or inductively expresses VSV enve-lope protein GP, collecting supernatant after 24 h to obtain the amplified VSV replication-defective virus, and measuring its titer; and (2) passaging the packaging cell 293T that transiently or stably or inductively expresses the coronavirus spike protein into a 60 mm dish, adding dVSVΔG-Fluc-EGFP, wherein multiplicity of infection MOI is 0.1 to 5, culturing in an incubator at 32° C. to 37° C., harvesting pseudovirus supernatant after 24 h, then treating with anti-VSV neutralizing antibody for 2 h, and filtering with 0.22 μm filter membrane to obtain coronavirus pseudovirus.

5. A coronavirus pseudovirus packaged by the coronavirus pseudovirus packaging system according to claim 1 as a biological indicator to replace a wild-type coronavirus for detection and evaluation of efficacy of a biological and chemical substance and a physical treatment method for inhibiting and disinfecting coronavirus, wherein the substance and the method for inhibiting and disinfecting coronavirus comprise an anti-coronavirus neutralizing antibodies, macromolecule and small-molecule drugs, physical virucidal disinfection methods, and chemical virucidal disinfectants.

6. A method of evaluating efficacy of a virucidal disinfectant using a coronavirus pseudovirus, comprising the following steps:

(1) construction of virus-contaminated environment simulating distribution of a target virus under a virucidal disinfectant evaluation scene, including the existence of medium, temperature, humidity and gas disturbance, through analysis of virus contamination distribution models;

diluting the packaged coronavirus pseudovirus, uniformly smearing the diluted coronavirus pseudovirus on a medium, and setting environmental parameters of evaluation scenarios;

(2) determination of concentration of coronavirus pseudovirus before virucidal disinfection treatment based on the evaluation requirements, performing standard virus characteristic detection before treatment with sampling the coronavirus pseudovirus at different positions and different points; and (3) sampling and determination during and after virucidal disinfection treatment uniformly spraying or smearing the virucidal disinfectant on the medium;

based on the evaluation requirements, selecting the positions and points selected in the step (2), sampling the coronavirus pseudovirus at different times, and detecting titer activity of the coronavirus pseudovirus.

7. The method according to claim 6, wherein the virus-contaminated environment in the step (1) comprises a logistics environment, a home environment, a public place environment, and a school environment.

8. The method according to claim 6, wherein multiple experimental groups are constructed in the step (1) to avoid excessive errors, and the step (3) comprises observing expression of fluorescent protein and luciferase after 293T-hACE2 is infected by the pseudovirus for measurement and calculation of infection capacity and bioactivity titer (TCID50 method, unit: PFU/ml) of the pseudovirus as well as detection of copy number of the pseudovirus nucleic acid (PCR method).

9. The method according to claim 6, wherein the virucidal disinfectant (peroxides, quaternary ammonium salts, chlorine-containing compounds, and alcohols) and the physical treatment method in the step (3) comprises combinations of one or more of ozone, peroxyacetic acid, hydrogen peroxide, chlorine dioxide, oxydol, sodium dichloroisocyanurate, ultraviolet light, negative ions, irradiation, or the like.

10. The method according to claim 6, wherein the medium in the step (1) and step (3) comprises one or more of a plastic, a foam, a bookbinding paperboard, a boxboard, a textile, and a metal foil.

* * * * *

SEQUENCE LISTING

<160> NUMBER OF SEQ ID NOS: 21

<210> SEQ ID NO 1
<211> LENGTH: 720
<212> TYPE: DNA
<213> ORGANISM: Artificial Sequence
<220> FEATURE:
<223> OTHER INFORMATION: Sequence of the fluorescent protein reporter
      gene

<400> SEQUENCE: 1

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

<210> SEQ ID NO 2
<211> LENGTH: 1659
<212> TYPE: DNA
<213> ORGANISM: Artificial Sequence
<220> FEATURE:
<223> OTHER INFORMATION: Sequence of the firefly luciferase Fluc gene

<400> SEQUENCE: 2

```
atggaagatg ccaagaacat caagaaaggc cctgccccct tctaccccct ggaagatggc      60
acagccggcg agcagctgca caaggccatg aagagatacg ccctggtgcc cggcaccatc     120
gccttcaccg acgcccacat cgaggtggac atcacctacg ccgagtattt cgagatgagc     180
```

-continued

```
gtgcggctgg ccgaggccat gaaacgctac ggcctgaaca ccaaccaccg gatcgtggtg      240
tgcagcgaga acagcctgca gttcttcatg cccgtgctgg gcgccctgtt catcggcgtg      300
gccgtggccc ctgccaacga catctacaac gagcgggagc tgctgaacag catgggcatc      360
agccagccca ccgtggtgtt cgtgagcaag aagggcctgc agaaaatcct gaacgtgcag      420
aagaagctgc ccatcatcca gaaaatcatc atcatggaca gcaagaccga ctaccagggc      480
ttccagagca tgtacacctt cgtgaccagc cacctgcccc ctggcttcaa cgagtacgac      540
ttcgtgcccg agagcttcga ccgggacaag accatcgccc tgatcatgaa cagcagcggc      600
agcaccggcc tgcctaaagg cgtggccctg cctcaccgga ccgcctgcgt gcggttcagc      660
cacgcccggg accccatctt cggcaaccag atcatccccg acaccgccat cctgagcgtg      720
gtgcccttcc accacggctt cggcatgttc accaccctgg gctacctgat ctgcggcttc      780
cgggtggtgc tgatgtaccg gttcgaggaa gagctgttcc tgcggagcct gcaggactac      840
aagatccaga cgccctgct ggtgcccacc ctgttcagct ttttcgccaa gagcaccctg      900
atcgacaagt acgacctgag caacctgcac gagatcgcca cggcggagc cccctgtcc      960 aaagaagtgg cgaagccgt cgccaagcgg ttccacctgc ccggcatccg gcagggctat     1020
ggcctgaccg agaccacaag cgccattctg atcacccccg agggcgacga caagcctggc     1080
gccgtgggca aggtggtgcc tttcttcgag gccaaggtgg tggacctgga caccggcaag     1140
accctgggcg tgaaccagcg gggcgagctg tgcgtgaggg gccccatgat catgagcggc     1200
tacgtgaaca accccgaggc caccaacgcc ctgattgaca aggacggctg gctgcacagc     1260
ggcgacatcg cctactggga cgaggacgag cacttcttca tcgtggaccg gctgaagagc     1320
ctgatcaagt acaagggcta ccaggtggcc cagccgagc tggaaagcat cctgctgcag     1380 cacccccaaca tcttcgatgc cgggggtggcc ggactgcccg acgacgatgc cggcgagctg     1440
cctgccgccg tggtggtgct ggaacacggc aaaaccatga ccgagaaaga aatcgtggac     1500
tacgtggcca gccaggtgac caccgccaag aaactgagag cggcgtggt gtttgtggac     1560 gaggtgccca agggcctgac aggcaagctg gacgcccgga agatccggga gatcctgatc     1620
aaggccaaga agggcggcaa gggcggcggc ggcagctaa                             1659
```

<210> SEQ ID NO 3
<211> LENGTH: 15443
<212> TYPE: DNA
<213> ORGANISM: Artificial Sequence
<220> FEATURE:
<223> OTHER INFORMATION: Sequence of dVSVdeltaG-Fluc-EGFP

<400> SEQUENCE: 3

```
tttaattttt atgaaaaaaa ctaacagcaa tcatggaagt ccacgatttt gagaccgacg      60
agttcaatga tttcaatgaa gatgactatg ccacaagaga attcctgaat cccgatgagc     120
gcatgacgta cttgaatcat gctgattaca acctgaattc tcctctaatt agtgatgata     180
ttgacaattt aatcaggaaa ttcaattctc ttccaattcc ctcgatgtgg gatagtaaga     240
actgggatgg agttcttgag atgttaacgt catgtcaagc caatcccatc ccaacatctc     300
agatgcataa atggatggga agttggttaa tgtctgataa tcatgatgcc agtcaagggt     360 atagttttt acatgaagtg gacaaagagg cagaaataac atttgacgtg gtggagacct     420
tcatccgcgg ctggggcaac aaaaccaattg aatacatcaa aaaggaaaga tggactgact     480
cattcaaaat tctcgcttat ttgtgtcaaa agttttttgga cttacacaag ttgacattaa     540
```

-continued

```
tcttaaatgc tgtctctgag gtggaattgc tcaacttggc gaggactttc aaaggcaaag     600
tcagaagaag ttctcatgga acgaacatat gcaggattag ggttcccagc ttgggtccta     660
cttttatttc agaaggatgg gcttacttca agaaacttga tattctaatg gaccgaaact     720
ttctgttaat ggtcaaagat gtgattatag ggaggatgca aacggtgcta tccatggtat     780
gtagaataga caacctgttc tcagagcaag acatcttctc ccttctaaat atctacagaa     840
ttggagataa aattgtggag aggcagggaa atttttctta tgacttgatt aaaatggtgg     900
aaccgatatg caacttgaag ctgatgaaat tagcaagaga atcaaggcct ttagtcccac     960
aattccctca ttttgaaaat catatcaaga cttctgttga tgaaggggca aaaattgacc    1020
gaggtataag attcctccat gatcagataa tgagtgtgaa aacagtggat ctcacactgg    1080
tgatttatgg atcgttcaga cattggggtc atccttttat agattattac actggactag    1140
aaaaattaca ttcccaagta accatgaaga aagatattga tgtgtcatat gcaaaagcac    1200
ttgcaagtga tttagctcgg attgttctat ttcaacagtt caatgatcat aaaaagtggt    1260
tcgtgaatgg agacttgctc cctcatgatc atccctttaa aagtcatgtt aaagaaaata    1320
catggcccac agctgctcaa gttcaagatt ttggagataa atggcatgaa cttccgctga    1380
ttaaatgttt tgaaataccc gacttactag acccatcgat aatatactct gacaaaagtc    1440
attcaatgaa taggtcagag gtgttgaaac atgtccgaat gaatccgaac actcctatcc    1500
ctagtaaaaa ggtgttgcag actatgttgg acacaaaggc taccaattgg aaagaatttc    1560
ttaaagagat tgatgagaag ggcttagatg atgatgatct aattattggt cttaaaggaa    1620
aggagaggga actgaagttg gcaggtagat ttttctccct aatgtcttgg aaattgcgag    1680
aatactttgt aattaccgaa tatttgataa agactcattt cgtccctatg tttaaaggcc    1740
tgacaatggc ggacgatcta actgcagtca ttaaaaagat gttagattcc tcatccggcc    1800
aaggattgaa gtcatatgag gcaatttgca tagccaatca cattgattac gaaaaatgga    1860
ataaccacca aaggaagtta tcaaacggcc cagtgttccg agttatgggc cagttcttag    1920
gttatccatc cttaatcgag agaactcatg aatttttttga gaaaagtctt atatactaca    1980
atggaagacc agacttgatg cgtgttcaca acaacacact gatcaattca acctcccaac    2040
gagtttgttg gcaaggacaa gagggtggac tggaaggtct acggcaaaaa ggatggagta    2100
tcctcaatct actggttatt caaagagagg ctaaaatcag aaacactgct gtcaaagtct    2160
tggcacaagg tgataatcaa gttatttgca cacagtataa aacgaagaaa tcgagaaacg    2220
ttgtagaatt acagggtgct ctcaatcaaa tggtttctaa taatgagaaa attatgactg    2280
caatcaaaat agggacaggg aagttaggac ttttgataaa tgacgatgag actatgcaat    2340
ctgcagatta cttgaattat ggaaaaatac cgattttccg tggagtgatt agagggttag    2400
agaccaagag atggtcacga gtgacttgtg tcaccaatga ccaaataccc acttgtgcta    2460
atataatgag ctcagtttcc acaaatgctc tcaccgtagc tcattttgct gagaacccaa    2520
tcaatgccat gatacagtac aattattttg ggacatttgc tagactcttg ttgatgatgc    2580
atgatcctgc tcttcgtcaa tcattgtatg aagttcaaga taagataccg ggcttgcaca    2640
gttctacttt caaatacgcc atgttgtatt tggaccttc cattggagga gtgtcgggca    2700
tgtctttgtc caggtttttg attagagcct tcccagatcc cgtaacagaa agtctctcat    2760
tctggagatt catccatgta catgctcgaa gtgagcatct gaaggagatg agtgcagtat    2820
ttggaaaccc cgagatagcc aagtttcgaa taactcacat agacaagcta gtagaagatc    2880
caacctctct gaacatcgct atgggaatga gtccagcgaa cttgttaaag actgaggtta    2940
```

-continued

```
aaaaatgctt aatcgaatca agacaaacca tcaggaacca ggtgattaag gatgcaacca      3000
tatatttgta tcatgaagag gatcggctca gaagtttctt atggtcaata aatcctctgt      3060
tccctagatt tttaagtgaa ttcaaatcag gcactttttt gggagtcgca gacgggctca      3120
tcagtctatt tcaaaattct cgtactattc ggaactcctt taagaaaaag tatcataggg      3180
aattggatga tttgattgtg aggagtgagg tatcctcttt gacacattta gggaaacttc      3240
atttgagaag gggatcatgt aaaatgtgga catgttcagc tactcatgct gacacattaa      3300
gatacaaatc ctggggccgt acagttattg ggacaactgt accccatcca ttagaaatgt      3360
tgggtccaca acatcgaaaa gagactcctt gtgcaccatg taacacatca gggttcaatt      3420
atgtttctgt gcattgtcca gacgggatcc atgacgtctt tagttcacgg ggaccattgc      3480
ctgcttatct agggtctaaa acatctgaat ctacatctat tttgcagcct tgggaaaggg      3540
aaagcaaagt cccactgatt aaaagagcta cacgtcttag agatgctatc tcttggtttg      3600
ttgaacccga ctctaaacta gcaatgacta tactttctaa catccactct ttaacaggcg      3660
aagaatggac caaaaggcag catgggttca aaagaacagg gtctgccctt cataggtttt      3720
cgacatctcg gatgagccat ggtgggttcg catctcagag cactgcagca ttgaccaggt      3780
tgatggcaac tacagacacc atgagggatc tgggagatca gaatttcgac tttttattcc      3840
aagcaacgtt gctctatgct caaattacca ccactgttgc aagagacgga tggatcacca      3900
gttgtacaga tcattatcat attgcctgta agtcctgttt gagacccata gaagagatca      3960
ccctggactc aagtatggac tacacgcccc cagatgtatc ccatgtgctg aagacatgga      4020
ggaatgggga aggttcgtgg ggacaagaga taaaacagat ctatccttta gaagggaatt      4080
ggaagaattt agcacctgct gagcaatcct atcaagtcgg cggatgtata ggttttctat      4140
atggagactt ggcgtataga aaatctactc atgccgagga cagttctcta tttcctctat      4200
ctatacaagg tcgtattaga ggtcgaggtt tcttaaaagg gttgctagac ggattaatga      4260
gagcaagttg ctgccaagta atacaccgga gaagtctggc tcatttgaag aggccggcca      4320
acgcagtgta cggaggtttg atttacttga ttgataaatt gagtgtatca cctccattcc      4380
tttctcttac tagatcagga cctattagag acgaattaga aacgattccc cacaagatcc      4440
caacctccta tccgacaagc aaccgtgata tgggggtgat tgtcagaaat tacttcaaat      4500
accaatgccg tctaattgaa aagggaaaat acagatcaca ttattcacaa ttatggttat      4560
tctcagatgt cttatccata gacttcattg gaccattctc tatttccacc accctcttgc      4620
aaatcctata caagccattt ttatctggga aagataagag tgagttgaga gagctggcaa      4680
atctttcttc attgctaaga tcaggagagg ggtgggaaga catacatgtg aaaattcttca     4740 ccaaggacat attattgtgt ccagaggaaa tcagacatgc ttgcaagttc gggattgcta      4800
aggataataa taaagacatg agctatcccc cttggggaag ggaatccaga gggacaatta      4860
caacaatccc tgtttattat acgaccaccc cttacccaaa gatgctagag atgcctccaa      4920
gaatccaaaa tcccctgctg tccggaatca ggttgggcca attaccaact ggcgctcatt      4980
ataaaattcg gagtatatta catggaatgg gaatccatta cagggacttc ttgagttgtg      5040
gagacggctc cggagggatg actgctgcat tactacgaga aaatgtgcat agcagaggaa      5100
tattcaatag tctgttagaa ttatcagggt cagtcatgcg aggcgcctct cctgagcccc      5160
ccagtgccct agaaactta ggaggagata aatcgagatg tgtaaatggt gaaacatgtt      5220
gggaatatcc atctgactta tgtgacccaa ggacttggga ctatttcctc cgactcaaag      5280
```

-continued

```
caggcttggg gcttcaaatt gatttaattg taatggatat ggaagtgcgg gattcttcta    5340
ctagcctgaa aattgagacg aatgttagaa attatgtgca ccggattttg gatgagcaag    5400 gagtttaat ctacaagact tatggaacat atatttgtga gagcgaaaag aatgcagtaa     5460
caatccttgg tcccatgttc aagacggtcg acttagttca aacagaattt agtagttctc    5520
aaacgtctga agtatatatg gtatgtaaag gtttgaagaa attaatcgat gaacccaatc    5580
ccgattggtc ttccatcaat gaatcctgga aaaacctgta cgcattccag tcatcagaac    5640
aggaatttgc cagagcaaag aaggttagta catactttac cttgacaggt attccctccc    5700
aattcattcc tgatcctttt gtaaacattg agactatgct acaaatattc ggagtaccca    5760
cgggtgtgtc tcatgcggct gccttaaaat catctgatag acctgcagat ttattgacca    5820
ttagcctttt ttatatggcg attatatcgt attataacat caatcatatc agagtaggac    5880
cgatacctcc gaacccccca tcagatggaa ttgcacaaaa tgtggggatc gctataactg    5940
gtataagctt ttggctgagt ttgatggaga aagacattcc actatatcaa cagtgtttag    6000
cagttatcca gcaatcattc ccgattaggt gggaggctgt ttcagtaaaa ggaggataca    6060
agcagaagtg gagtactaga ggtgatgggc tcccaaaaga tacccgaatt tcagactcct    6120
tggccccaat cgggaactgg atcagatctc tggaattggt ccgaaaccaa gttcgtctaa    6180
atccattcaa tgagatcttg ttcaatcagc tatgtcgtac agtggataat catttgaaat    6240
ggtcaaattt gcgaagaaac acaggaatga ttgaatggat caatagacga atttcaaaag    6300
aagaccggtc tatactgatg ttgaagagtg acctacacga ggaaaactct tggagagatt    6360
aaaaaatcat gaggagactc caaactttaa gtatgaaaaa aactttgatc cttaagaccc    6420
tcttgtggtt tttattttt atctggtttt gtggtcttcg tgggtcggca tggcatctcc     6480
acctcctcgc ggtccgacct gggcatccga aggaggacgt cgtccactcg gatggctaag    6540
ggaggggccc ccgcggggct gctaacaaag cccgaaagga agctgagttg gctgctgcca    6600
ccgctgagca ataactagca taaccccttg gggcctctaa acgggtcttg aggggttttt    6660
tgctgaaagg aggaactata tccggatcga gacctcgata ctagtattgc gttgcgctca    6720
ctgcccgctt tccagtcggg aaacctgtcg tgccagctgc attaatgaat cggccaacgc    6780
gcggggagag gcggtttgcg tagagccaat caattcttgc ggagaactgt gaatgcgcaa    6840
accaaccctt ggcagaacat atccatcgcg tccgccatct ccagcagccg cacgcggcgc    6900
atctcgggca gcgttgggtc ctggccacgg gtgcgcatga tcgtgctcct gtcgttgagg    6960
acccggctag gctggcgggg ttgccttact ggttagcaga atgaatcacc gatacgcgag    7020
cgaacgtgaa gcgactgctg ctgcaaaacg tctgcgacct gagcaacaac atgaatggtc    7080
ttcggtttcc gtgtttcgta aagtctggaa acgcggaagt cagcgccctg caccattatg    7140
ttccggatct gcatcgcagg atgctgctgg ctaccctgtg gaacacctac atctgtatta    7200
acgaagcgct ggcattgacc ctgagtgatt tttctctggt cccgccgcat ccataccgcc    7260
agttgtttac cctcacaacg ttccagtaac cgggcatgtt catcatcagt aacccgtatc    7320
gtgagcatcc tctctcgttt catcggtatc attacccccca tgaacagaaa tcccccttac   7380
acggaggcat cagtgaccaa acaggaaaaa accgccctta acatggcccg ctttatcaga    7440
agccagacat taacgcttct ggagaaactc aacgagctgg acgcggatga acaggcagac    7500
atctgtgaat cgcttcacga ccacgctgat gagctttacc gcagctgcct cgcgcgtttc    7560
ggtgatgacg gtgaaaacct ctgacacatg cagctcccgg agacggtcac agcttgtctg    7620
taagcggatg ccgggagcag acaagcccgt cagggcgcgt cagcgggtgt tggcgggtgt    7680
```

```
cggggcgcag ccatgaccca gtcacgtagc gatagcggag tgtatactgg cttaactatg   7740
cggcatcaga gcagattgta ctgagagtgc accatatgcg gtgtgaaata ccgcacagat   7800
gcgtaaggag aaaataccgc atcaggcgct cttccgcttc ctcgctcact gactcgctgc   7860
gctcggtcgt tcggctgcgg cgagcggtat cagctcactc aaaggcggta atacggttat   7920
ccacagaatc aggggataac gcaggaaaga acatgtgagc aaaaggccag caaaaggcca   7980
ggaaccgtaa aaaggccgcg ttgctggcgt ttttccatag gctccgcccc cctgacgagc   8040
atcacaaaaa tcgacgctca agtcagaggt ggcgaaaccc gacaggacta taaagatacc   8100
aggcgtttcc ccctggaagc tccctcgtgc gctctcctgt tccgaccctg ccgcttaccg   8160
gatacctgtc cgcctttctc ccttcgggaa gcgtggcgct ttctcatagc tcacgctgta   8220
ggtatctcag ttcggtgtag gtcgttcgct ccaagctggg ctgtgtgcac gaaccccccg   8280
ttcagcccga ccgctgcgcc ttatccggta actatcgtct tgagtccaac ccggtaagac   8340
acgacttatc gccactggca gcagccactg gtaacaggat tagcagagcg aggtatgtag   8400
gcggtgctac agagttcttg aagtggtggc ctaactacgg ctacactaga aggacagtat   8460
ttggtatctg cgctctgctg aagccagtta ccttcggaaa aagagttggt agctcttgat   8520
ccggcaaaca aaccaccgct ggtagcggtg gttttttttgt ttgcaagcag cagattacgc   8580
gcagaaaaaa aggatctcaa gaagatcctt tgatcttttc tacggggtct gacgctcagt   8640
ggaacgaaaa ctcacgttaa gggattttgg tcatgagatt atcaaaaagg atcttcacct   8700
agatcctttt aaattaaaaa tgaagtttta aatcaatcta agtatatat gagtaaactt   8760 ggtctgacag ttagaaaaac tcatcgagca tcaaatgaaa ctgcaattta ttcatatcag   8820
gattatcaat accatatttt tgaaaaagcc gtttctgtaa tgaaggagaa aactcaccga   8880
ggcagttcca taggatggca agatcctggt atcggtctgc gattccgact cgtccaacat   8940
caatacaacc tattaatttc ccctcgtcaa aaataaggtt atcaagtgag aaatcaccat   9000
gagtgacgac tgaatccggt gagaatggca aaagtttatg catttctttc cagacttgtt   9060
caacaggcca gccattacgc tcgtcatcaa aatcactcgc atcaaccaaa ccgttattca   9120
ttcgtgattg cgcctgagcg agacgaaata cgcgatcgct gttaaaagga caattacaaa   9180
caggaatcga atgcaaccgg cgcaggaaca ctgccagcgc atcaacaata ttttcacctg   9240
aatcaggata ttcttctaat acctggaatg ctgtttttccc agggatcgca gtggtgagta   9300
accatgcatc atcaggagta cggataaaat gcttgatggt cggaagaggc ataaattccg   9360
tcagccagtt tagtctgacc atctcatctg taacatcatt ggcaacgcta cctttgccat   9420
gtttcagaaa caactctggc gcatcgggct tcccatacaa tcgatagatt gtcgcacctg   9480
attgcccgac attatcgcga gcccatttat acccatataa atcagcatcc atgttggaat   9540
ttaatcgcgg cctagagcaa gacgtttccc gttgaatatg gctcatactc ttccttttttc   9600 aatattattg aagcatttat cagggttatt gtctcatgag cggatacata tttgaatgta   9660
tttagaaaaa taaacaaata ggggttccgc gcacatttcc ccgaaaagtg ccacctgcga   9720
tcggtgcggg cctcttcgct attacgccag ctggcgaaag ggggatgtgc tgcaaggcga   9780
ttaagttggg taacgccagg gttttcccag tcacgacgtt gtaaaacgac ggccagtgaa   9840
ttgtaatacg actcactata ggacgaagac aaacaaacca ttattatcat taaaaggctc   9900
aggagaaact ttaacagtaa tcaaaatgtc tgttacagtc aagagaatca ttgacaacac   9960
agtcgtagtt ccaaaacttc ctgcaaatga ggatccagtg gaatacccgg cagattactt   10020
```

-continued

```
cagaaaatca aaggagattc ctctttacat caatactaca aaaagtttgt cagatctaag    10080
aggatatgtc taccaaggcc tcaaatccgg aaatgtatca atcatacatg tcaacagcta    10140
cttgtatgga gcattaaagg acatccgggg taagttggat aaagattggt caagtttcgg    10200
aataaacatc gggaaagcag gggatacaat cggaatattt gaccttgtat ccttgaaagc    10260
cctggacggc gtacttccag atggagtatc ggatgcttcc agaaccagcg cagatgacaa    10320
atggttgcct ttgtatctac ttggcttata cagagtgggc agaacacaaa tgcctgaata    10380
cagaaaaaag ctcatggatg ggctgacaaa tcaatgcaaa atgatcaatg aacagtttga    10440
acctcttgtg ccagaaggtc gtgacatttt tgatgtgtgg ggaaatgaca gtaattacac    10500
aaaaattgtc gctgcagtgg acatgttctt ccacatgttc aaaaaacatg aatgtgcctc    10560
gttcagatac ggaactattg tttccagatt caaagattgt gctgcattgg caacatttgg    10620
acacctctgc aaaataaccg gaatgtctac agaagatgta acgacctgga tcttgaaccg    10680
agaagttgca gatgaaatgg tccaaatgat gcttccaggc caagaaattg acaaggccga    10740
ttcatacatg ccttatttga tcgactttgg attgtcttct aagtctccat attcttccgt    10800
caaaaaccct gccttccact tctgggggca attgacagct cttctgctca gatccaccag    10860
agcaaggaat gcccgacagc ctgatgacat tgagtataca tctcttacta cagcaggttt    10920
gttgtacgct tatgcagtag gatcctctgc cgacttggca caacagtttt gtgttggaga    10980
taacaaatac actccagatg atagtaccgg aggattgacg actaatgcac cgccacaagg    11040
cagagatgtg gtcgaatggc tcggatggtt tgaagatcaa aacagaaaac cgactcctga    11100
tatgatgcag tatgcgaaaa gagcagtcat gtcactgcaa ggcctaagag agaagacaat    11160
tggcaagtat gctaagtcag aatttgacaa atgaccctat aattctcaga tcacctatta    11220
tatattatgc tacatatgaa aaaaactaac agatatcatg gataatctca caaaagttcg    11280
tgagtatctc aagtcctatt ctcgtctgga tcaggcggta ggagagatag atgagatcga    11340
agcacaacga gctgaaaagt ccaattatga gttgttccaa gaggatggag tggaagagca    11400
tactaagccc tcttattttc aggcagcaga tgattctgac acagaatctg aaccagaaat    11460
tgaagacaat caaggcttgt atgcaccaga tccagaagct gagcaagttg aaggctttat    11520
acaggggcct ttagatgact atgcagatga ggaagtggat gttgtattta cttcggactg    11580
gaaacagcct gagcttgaat ctgacgagca tggaaagacc ttacggttga catcgccaga    11640
gggtttaagt ggagagcaga aatcccagtg gctttcgacg attaaagcag tcgtgcaaag    11700
tgccaaatac tggaatctgg cagagtgcac atttgaagca tcgggagaag gggtcattat    11760
gaaggagcgc cagataactc cggatgtata taaggtcact ccagtgatga acacacatcc    11820
gtcccaatca gaagcagtat cagatgtttg gtctctctca aagacatcca tgactttcca    11880
acccaagaaa gcaagtcttc agcctctcac catatccttg gatgaattgt tctcatctag    11940
aggagagttc atctctgtcg gaggtgacgg acgaatgtct cataaagagg ccatcctgct    12000
cggcctgaga tacaaaaagt tgtacaatca ggcgagagtc aaatattctc tgtagactat    12060
gaaaaaaagt aacagatatc acgatctaag tgttatccca atccattcat catgagttcc    12120
ttaaagaaga ttctcggtct gaaggggaaa ggtaagaaat ctaagaaatt agggatcgca    12180 ccacccccctt atgaagagga cactagcatg gagtatgctc cgagcgctcc aattgacaaa    12240
tcctattttg gagttgacga gatggacacc tatgatccga atcaattaag atatgagaaa    12300
ttcttcttta cagtgaaaat gacgttaga tctaatcgtc cgttcagaac atactcagat    12360
gtggcagccg ctgtatccca ttgggatcac atgtacatcg gaatggcagg gaaacgtccc    12420
```

-continued

```
ttctacaaaa tcttggcttt tttgggttct tctaatctaa aggccactcc agcggtattg    12480
gcagatcaag gtcaaccaga gtatcacgct cactgcgaag gcagggctta tttgccacat    12540
aggatgggga agacccctcc catgctcaat gtaccagagc acttcagaag accattcaat    12600
ataggtcttt acaagggaac gattgagctc acaatgacca tctacgatga tgagtcactg    12660
gaagcagctc ctatgatctg ggatcatttc aattcttcca aattttctga tttcagagag    12720
aaggccttaa tgtttggcct gattgtcgag aaaaaggcat ctggagcgtg ggtcctggac    12780
tctatcggcc acttcaaatg agctagtcta acttctagct tctgaacaat ccccggttta    12840
ctcagtctcc cctaattcca gcctctcgaa caactaatat cctgtctttt ctatccctat    12900
gaaaaaaact aacagagatc gatctgttta cgcgtcacta tggaagatgc caagaacatc    12960
aagaaaggcc ctgccccctt ctaccccctg gaagatggca cagccggcga gcagctcac    13020 aaggccatga agagatacgc cctggtgccc ggcaccatcg ccttcaccga cgcccacatc    13080
gaggtggaca tcacctacgc cgagtatttc gagatgagcg tgcggctggc cgaggccatg    13140
aaacgctacg gcctgaacac caaccaccgg atcgtggtgt gcagcgagaa cagcctgcag    13200
ttcttcatgc ccgtgctggg cgccctgttc atcggcgtgg ccgtggcccc tgccaacgac    13260
atctacaacg agcgggagct gctgaacagc atgggcatca gccagcccac cgtggtgttc    13320
gtgagcaaga agggcctgca gaaaatcctg aacgtgcaga agaagctgcc catcatccag    13380
aaaatcatca tcatggacag caagaccgac taccagggct tccagagcat gtacaccttc    13440
gtgaccagcc acctgccccc tggcttcaac gagtacgact tcgtgcccga gagcttcgac    13500
cgggacaaga ccatcgccct gatcatgaac agcagcggca gcaccggcct gcctaaaggc    13560
gtggccctgc ctcaccggac cgcctgcgtg cggttcagcc acgcccggga ccccatcttc    13620
ggcaaccaga tcatccccga caccgccatc ctgagcgtgg tgcccttcca ccacggcttc    13680
ggcatgttca ccaccctggg ctacctgatc tgcggcttcc gggtggtgct gatgtaccgg    13740
ttcgaggaag agctgttcct gcggagcctg caggactaca agatccagag cgccctgctg    13800
gtgcccaccc tgttcagctt tttcgccaag agcaccctga tcgacaagta cgacctgagc    13860
aacctgcacg agatcgccag cggcggagcc cccctgtcca aagaagtggg cgaagccgtc    13920
gccaagcggt tccacctgcc cggcatccgg cagggctatg gcctgaccga gaccacaagc    13980
gccattctga tcacccccga gggcgacgac aagcctggcg ccgtgggcaa ggtggtgcct    14040
ttcttcgagg ccaaggtggt ggacctggac accggcaaga ccctgggcgt gaaccagcgg    14100
ggcgagctgt gcgtgagggg ccccatgatc atgagcggct acgtgaacaa ccccgaggcc    14160
accaacgccc tgattgacaa ggacggctgg ctgcacagcg gcgacatcgc ctactgggac    14220
gaggacgagc acttcttcat cgtggaccgg ctgaagagcc tgatcaagta caagggctac    14280
caggtggccc cagccgagct ggaaagcatc ctgctgcagc accccaacat cttcgatgcc    14340
ggggtggccg gactgcccga cgacgatgcc ggcgagctgc ctgccgccgt ggtggtgctg    14400
gaacacggca aaaccatgac cgagaaagaa atcgtggact acgtggccag ccaggtgacc    14460
accgccaaga aactgagagg cggcgtggtg tttgtggacg aggtgcccaa gggcctgaca    14520
ggcaagctgg acgcccggaa gatccgggag atcctgatca aggccaagaa gggcggcaag    14580
ggcggcggcg gcagctaact caaatcctgc taggtatgaa aaaaactaac agatatcacg    14640
ctcgagatgg tgagcaaggg cgaggagctg ttcaccgggg tggtgcccat cctggtcgag    14700
ctggacggcg acgtaaacgg ccacaagttc agcgtgtccg gcgagggcga gggcgatgcc    14760
```

```
acctacggca agctgaccct gaagttcatc tgcaccaccg gcaagctgcc cgtgccctgg   14820
cccaccctcg tgaccaccct gacctacggc gtgcagtgct tcagccgcta ccccgaccac   14880
atgaagcagc acgacttctt caagtccgcc atgcccgaag ctacgtcca ggagcgcacc    14940 atcttcttca aggacgacgg caactacaag acccgcgccg aggtgaagtt cgagggcgac   15000
accctggtga accgcatcga gctgaagggc atcgacttca aggaggacgg caacatcctg   15060
gggcacaagc tggagtacaa ctacaacagc cacaacgtct atatcatggc cgacaagcag   15120
aagaacggca tcaaggtgaa cttcaagatc cgccacaaca tcgaggacgg cagcgtgcag   15180
ctcgccgacc actaccagca gaacacccc atcggcgacg ccccgtgct gctgcccgac     15240 aaccactacc tgagcaccca gtccgccctg agcaaagacc ccaacgagaa gcgcgatcac   15300
atggtcctgc tggagttcgt gaccgccgcc gggatcactc tcggcatgga cgagctgtac   15360
aagtaagcta gccagattct tcatgtttgg accaaatcaa cttgtgatac catgctcaaa   15420
gaggcctcaa ttatatttga gtt                                         15443
```

```
<210> SEQ ID NO 4
<211> LENGTH: 1236
<212> TYPE: PRT
<213> ORGANISM: Artificial Sequence
<220> FEATURE:
<223> OTHER INFORMATION: Sequence obtained deletion of 19 amino acids at
      3' end of the SARS coronavirus spike protein S

<400> SEQUENCE: 4

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Asp Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240
```

-continued

```
Ala Gln Asp Thr Trp Gly Thr Ser Ala Ala Ala Tyr Phe Val Gly Tyr
            245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
            290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
            405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655
```

```
Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
            995                 1000                 1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
    1025                 1030                 1035

Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
```

-continued

```
         1070            1075            1080

Trp Phe  Ile Thr Gln Arg Asn  Phe Phe Ser Pro Gln  Ile Ile Thr
    1085            1090            1095

Thr Asp  Asn Thr Phe Val Ser  Gly Asn Cys Asp Val  Val Ile Gly
    1100            1105            1110

Ile Ile  Asn Asn Thr Val Tyr  Asp Pro Leu Gln Pro  Glu Leu Asp
    1115            1120            1125

Ser Phe  Lys Glu Glu Leu Asp  Lys Tyr Phe Lys Asn  His Thr Ser
    1130            1135            1140

Pro Asp  Val Asp Leu Gly Asp  Ile Ser Gly Ile Asn  Ala Ser Val
    1145            1150            1155

Val Asn  Ile Gln Lys Glu Ile  Asp Arg Leu Asn Glu  Val Ala Lys
    1160            1165            1170

Asn Leu  Asn Glu Ser Leu Ile  Asp Leu Gln Glu Leu  Gly Lys Tyr
    1175            1180            1185

Glu Gln  Tyr Ile Lys Trp Pro  Trp Tyr Val Trp Leu  Gly Phe Ile
    1190            1195            1200

Ala Gly  Leu Met Ala Ile Val  Met Val Thr Ile Leu  Leu Cys Cys
    1205            1210            1215

Met Thr  Ser Cys Cys Ser Cys  Leu Lys Gly Ala Cys  Ser Cys Gly
    1220            1225            1230

Ser Cys  Cys
    1235
```

<210> SEQ ID NO 5
<211> LENGTH: 1334
<212> TYPE: PRT
<213> ORGANISM: Artificial Sequence
<220> FEATURE:
<223> OTHER INFORMATION: Sequence obtained after deletion of 19 amino
      acids at 3' end of the MERS coronavirus spike protein S

<400> SEQUENCE: 5

```
Met Ile His Ser Val Phe Leu Leu Met Phe Leu Leu Thr Pro Thr Glu
1               5               10              15

Ser Tyr Val Asp Val Gly Pro Asp Ser Val Lys Ser Ala Cys Ile Glu
            20              25              30

Val Asp Ile Gln Gln Thr Phe Phe Asp Lys Thr Trp Pro Arg Pro Ile
        35              40              45

Asp Val Ser Lys Ala Asp Gly Ile Ile Tyr Pro Gln Gly Arg Thr Tyr
        50              55              60

Ser Asn Ile Thr Ile Thr Tyr Gln Gly Leu Phe Pro Tyr Gln Gly Asp
65              70              75              80

His Gly Asp Met Tyr Val Tyr Ser Ala Gly His Ala Thr Gly Thr Thr
                85              90              95

Pro Gln Lys Leu Phe Val Ala Asn Tyr Ser Gln Asp Val Lys Gln Phe
            100             105             110

Ala Asn Gly Phe Val Val Arg Ile Gly Ala Ala Ala Asn Ser Thr Gly
            115             120             125

Thr Val Ile Ile Ser Pro Ser Thr Ser Ala Thr Ile Arg Lys Ile Tyr
        130             135             140

Pro Ala Phe Met Leu Gly Ser Ser Val Gly Asn Phe Ser Asp Gly Lys
145             150             155             160

Met Gly Arg Phe Phe Asn His Thr Leu Val Leu Leu Pro Asp Gly Cys
                165             170             175
```

```
Gly Thr Leu Leu Arg Ala Phe Tyr Cys Ile Leu Glu Pro Arg Ser Gly
        180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
        260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
        340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
        420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
        500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
        580                 585                 590

Asp Thr Lys Ile Ala Ser Gln Leu Gly Asn Cys Val Glu Tyr Ser Leu
```

-continued

```
            595                  600                  605

Tyr Gly Val Ser Gly Arg Gly Val Phe Gln Asn Cys Thr Ala Val Gly
    610                  615                  620

Val Arg Gln Gln Arg Phe Val Tyr Asp Ala Tyr Gln Asn Leu Val Gly
625                  630                  635                  640

Tyr Tyr Ser Asp Asp Gly Asn Tyr Tyr Cys Leu Arg Ala Cys Val Ser
                645                  650                  655

Val Pro Val Ser Val Ile Tyr Asp Lys Glu Thr Lys Thr His Ala Thr
                660                  665                  670

Leu Phe Gly Ser Val Ala Cys Glu His Ile Ser Ser Thr Met Ser Gln
                675                  680                  685

Tyr Ser Arg Ser Thr Arg Ser Met Leu Lys Arg Arg Asp Ser Thr Tyr
    690                  695                  700

Gly Pro Leu Gln Thr Pro Val Gly Cys Val Leu Gly Leu Val Asn Ser
705                  710                  715                  720

Ser Leu Phe Val Glu Asp Cys Lys Leu Pro Leu Gly Gln Ser Leu Cys
                725                  730                  735

Ala Leu Pro Asp Thr Pro Ser Thr Leu Thr Pro Arg Ser Val Arg Ser
                740                  745                  750

Val Pro Gly Glu Met Arg Leu Ala Ser Ile Ala Phe Asn His Pro Ile
                755                  760                  765

Gln Val Asp Gln Leu Asn Ser Ser Tyr Phe Lys Leu Ser Ile Pro Thr
    770                  775                  780

Asn Phe Ser Phe Gly Val Thr Gln Glu Tyr Ile Gln Thr Thr Ile Gln
785                  790                  795                  800

Lys Val Thr Val Asp Cys Lys Gln Tyr Val Cys Asn Gly Phe Gln Lys
                805                  810                  815

Cys Glu Gln Leu Leu Arg Glu Tyr Gly Gln Phe Cys Ser Lys Ile Asn
                820                  825                  830

Gln Ala Leu His Gly Ala Asn Leu Arg Gln Asp Asp Ser Val Arg Asn
                835                  840                  845

Leu Phe Ala Ser Val Lys Ser Ser Gln Ser Ser Pro Ile Ile Pro Gly
    850                  855                  860

Phe Gly Gly Asp Phe Asn Leu Thr Leu Leu Glu Pro Val Ser Ile Ser
865                  870                  875                  880

Thr Gly Ser Arg Ser Ala Arg Ser Ala Ile Glu Asp Leu Leu Phe Asp
                885                  890                  895

Lys Val Thr Ile Ala Asp Pro Gly Tyr Met Gln Gly Tyr Asp Asp Cys
                900                  905                  910

Met Gln Gln Gly Pro Ala Ser Ala Arg Asp Leu Ile Cys Ala Gln Tyr
                915                  920                  925

Val Ala Gly Tyr Lys Val Leu Pro Pro Leu Met Asp Val Asn Met Glu
    930                  935                  940

Ala Ala Tyr Thr Ser Ser Leu Leu Gly Ser Ile Ala Gly Val Gly Trp
945                  950                  955                  960

Thr Ala Gly Leu Ser Ser Phe Ala Ala Ile Pro Phe Ala Gln Ser Ile
                965                  970                  975

Phe Tyr Arg Leu Asn Gly Val Gly Ile Thr Gln Gln Val Leu Ser Glu
                980                  985                  990

Asn Gln Lys Leu Ile Ala Asn Lys  Phe Asn Gln Ala Leu  Gly Ala Met
            995                  1000                  1005

Gln Thr  Gly Phe Thr Thr Thr  Asn Glu Ala Phe Gln  Lys Val Gln
    1010                  1015                  1020
```

```
Asp Ala  Val Asn Asn Asn Ala  Gln Ala Leu Ser Lys  Leu Ala Ser
    1025             1030             1035

Glu Leu  Ser Asn Thr Phe Gly  Ala Ile Ser Ala Ser  Ile Gly Asp
    1040             1045             1050

Ile Ile  Gln Arg Leu Asp Val  Leu Glu Gln Asp Ala  Gln Ile Asp
    1055             1060             1065

Arg Leu  Ile Asn Gly Arg Leu  Thr Thr Leu Asn Ala  Phe Val Ala
    1070             1075             1080

Gln Gln  Leu Val Arg Ser Glu  Ser Ala Ala Leu Ser  Ala Gln Leu
    1085             1090             1095

Ala Lys  Asp Lys Val Asn Glu  Cys Val Lys Ala Gln  Ser Lys Arg
    1100             1105             1110

Ser Gly  Phe Cys Gly Gln Gly  Thr His Ile Val Ser  Phe Val Val
    1115             1120             1125

Asn Ala  Pro Asn Gly Leu Tyr  Phe Met His Val Gly  Tyr Tyr Pro
    1130             1135             1140

Ser Asn  His Ile Glu Val Val  Ser Ala Tyr Gly Leu  Cys Asp Ala
    1145             1150             1155

Ala Asn  Pro Thr Asn Cys Ile  Ala Pro Val Asn Gly  Tyr Phe Ile
    1160             1165             1170

Lys Thr  Asn Asn Thr Arg Ile  Val Asp Glu Trp Ser  Tyr Thr Gly
    1175             1180             1185

Ser Ser  Phe Tyr Ala Pro Glu  Pro Ile Thr Ser Leu  Asn Thr Lys
    1190             1195             1200

Tyr Val  Ala Pro Gln Val Thr  Tyr Gln Asn Ile Ser  Thr Asn Leu
    1205             1210             1215

Pro Pro  Pro Leu Leu Gly Asn  Ser Thr Gly Ile Asp  Phe Gln Asp
    1220             1225             1230

Glu Leu  Asp Glu Phe Phe Lys  Asn Val Ser Thr Ser  Ile Pro Asn
    1235             1240             1245

Phe Gly  Ser Leu Thr Gln Ile  Asn Thr Thr Leu Leu  Asp Leu Thr
    1250             1255             1260

Tyr Glu  Met Leu Ser Leu Gln  Gln Val Val Lys Ala  Leu Asn Glu
    1265             1270             1275

Ser Tyr  Ile Asp Leu Lys Glu  Leu Gly Asn Tyr Thr  Tyr Tyr Asn
    1280             1285             1290

Lys Trp  Pro Trp Tyr Ile Trp  Leu Gly Phe Ile Ala  Gly Leu Val
    1295             1300             1305

Ala Leu  Ala Leu Cys Val Phe  Phe Ile Leu Cys Cys  Thr Gly Cys
    1310             1315             1320

Gly Thr  Asn Cys Met Gly Lys  Leu Lys Cys Asn
    1325             1330
```

```
<210> SEQ ID NO 6
<211> LENGTH: 1254
<212> TYPE: PRT
<213> ORGANISM: Artificial Sequence
<220> FEATURE:
<223> OTHER INFORMATION: Sequence obtained after deletion of 19 amino
      acids at 3' end of the COVID-19 coronavirus spike protein

<400> SEQUENCE: 6

Met Phe Val Phe Leu Val Leu Leu Pro Leu Val Ser Ser Gln Cys Val
1                 5                  10                 15

Asn Leu Thr Thr Arg Thr Gln Leu Pro Pro Ala Tyr Thr Asn Ser Phe
```

```
                20                  25                  30
Thr Arg Gly Val Tyr Tyr Pro Asp Lys Val Phe Arg Ser Ser Val Leu
            35                  40                  45
His Ser Thr Gln Asp Leu Phe Leu Pro Phe Phe Ser Asn Val Thr Trp
        50                  55                  60
Phe His Ala Ile His Val Ser Gly Thr Asn Gly Thr Lys Arg Phe Asp
65                  70                  75                  80
Asn Pro Val Leu Pro Phe Asn Asp Gly Val Tyr Phe Ala Ser Thr Glu
                85                  90                  95
Lys Ser Asn Ile Ile Arg Gly Trp Ile Phe Gly Thr Thr Leu Asp Ser
                100                 105                 110
Lys Thr Gln Ser Leu Leu Ile Val Asn Asn Ala Thr Asn Val Val Ile
            115                 120                 125
Lys Val Cys Glu Phe Gln Phe Cys Asn Asp Pro Phe Leu Gly Val Tyr
            130                 135                 140
Tyr His Lys Asn Asn Lys Ser Trp Met Glu Ser Glu Phe Arg Val Tyr
145                 150                 155                 160
Ser Ser Ala Asn Asn Cys Thr Phe Glu Tyr Val Ser Gln Pro Phe Leu
                165                 170                 175
Met Asp Leu Glu Gly Lys Gln Gly Asn Phe Lys Asn Leu Arg Glu Phe
                180                 185                 190
Val Phe Lys Asn Ile Asp Gly Tyr Phe Lys Ile Tyr Ser Lys His Thr
            195                 200                 205
Pro Ile Asn Leu Val Arg Asp Leu Pro Gln Gly Phe Ser Ala Leu Glu
    210                 215                 220
Pro Leu Val Asp Leu Pro Ile Gly Ile Asn Ile Thr Arg Phe Gln Thr
225                 230                 235                 240
Leu Leu Ala Leu His Arg Ser Tyr Leu Thr Pro Gly Asp Ser Ser Ser
                245                 250                 255
Gly Trp Thr Ala Gly Ala Ala Ala Tyr Tyr Val Gly Tyr Leu Gln Pro
            260                 265                 270
Arg Thr Phe Leu Leu Lys Tyr Asn Glu Asn Gly Thr Ile Thr Asp Ala
            275                 280                 285
Val Asp Cys Ala Leu Asp Pro Leu Ser Glu Thr Lys Cys Thr Leu Lys
    290                 295                 300
Ser Phe Thr Val Glu Lys Gly Ile Tyr Gln Thr Ser Asn Phe Arg Val
305                 310                 315                 320
Gln Pro Thr Glu Ser Ile Val Arg Phe Pro Asn Ile Thr Asn Leu Cys
                325                 330                 335
Pro Phe Gly Glu Val Phe Asn Ala Thr Arg Phe Ala Ser Val Tyr Ala
            340                 345                 350
Trp Asn Arg Lys Arg Ile Ser Asn Cys Val Ala Asp Tyr Ser Val Leu
            355                 360                 365
Tyr Asn Ser Ala Ser Phe Ser Thr Phe Lys Cys Tyr Gly Val Ser Pro
    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
```

```
Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
            675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
    755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
    850             855             860
```

-continued

```
Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys
    1250
```

<210> SEQ ID NO 7
<211> LENGTH: 1263
<212> TYPE: PRT
<213> ORGANISM: Artificial Sequence
<220> FEATURE:
<223> OTHER INFORMATION: Sequence obtained after deletion of 19 amino
      acids at 3' end of the COVID-19 coronavirus spike protein S and
      fusion of HA protein

<400> SEQUENCE: 7

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65              70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145             150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

-continued

```
Tyr Asn Ser Ala Ser Phe Ser Thr Phe Lys Cys Tyr Gly Val Ser Pro
    370             375                 380

Thr Lys Leu Asn Asp Leu Cys Phe Thr Asn Val Tyr Ala Asp Ser Phe
385             390                 395                 400

Val Ile Arg Gly Asp Glu Val Arg Gln Ile Ala Pro Gly Gln Thr Gly
                405             410                 415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
    515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
    675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
    755             760             765

Gly Ile Ala Val Glu Gln Asp Lys Asn Thr Gln Glu Val Phe Ala Gln
    770             775             780
```

```
Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
```

-continued

```
      1190                1195                1200

Gly Lys  Tyr Glu Gln Tyr  Ile  Lys Trp Pro Trp Tyr  Ile Trp Leu
      1205                1210                1215

Gly Phe  Ile Ala Gly Leu  Ile  Ala Ile Val Met Val  Thr Ile Met
      1220                1225                1230

Leu Cys  Cys Met Thr Ser  Cys  Cys Ser Cys Leu Lys  Gly Cys Cys
      1235                1240                1245

Ser Cys  Gly Ser Cys Cys  Tyr  Pro Tyr Asp Val Pro  Asp Tyr Ala
      1250                1255                1260

<210> SEQ ID NO 8
<211> LENGTH: 27
<212> TYPE: DNA
<213> ORGANISM: Artificial Sequence
<220> FEATURE:
<223> OTHER INFORMATION: Primer COVID19-S-XhoI-F1

<400> SEQUENCE: 8
ccgctcgaga tgttcgtgtt tctggtg                                        27

<210> SEQ ID NO 9
<211> LENGTH: 30
<212> TYPE: DNA
<213> ORGANISM: Artificial Sequence
<220> FEATURE:
<223> OTHER INFORMATION: Primer COVID19-S-NheI-R1

<400> SEQUENCE: 9
ctagctagct taggtgtagt gcagcttcac                                     30

<210> SEQ ID NO 10
<211> LENGTH: 27
<212> TYPE: DNA
<213> ORGANISM: Artificial Sequence
<220> FEATURE:
<223> OTHER INFORMATION: Primer COVID19-S-C19-XhoI-F1

<400> SEQUENCE: 10
ccgctcgaga tgttcgtgtt tctggtg                                        27

<210> SEQ ID NO 11
<211> LENGTH: 33
<212> TYPE: DNA
<213> ORGANISM: Artificial Sequence
<220> FEATURE:
<223> OTHER INFORMATION: Primer COVID19-S-C19-NheI-R1

<400> SEQUENCE: 11
ctagctagct taacagcagc ttccacaaga aca                                 33

<210> SEQ ID NO 12
<211> LENGTH: 27
<212> TYPE: DNA
<213> ORGANISM: Artificial Sequence
<220> FEATURE:
<223> OTHER INFORMATION: Primer COVID19-S-C27-XhoI-F1

<400> SEQUENCE: 12
ccgctcgaga tgttcgtgtt tctggtg                                        27

<210> SEQ ID NO 13
<211> LENGTH: 34
<212> TYPE: DNA
<213> ORGANISM: Artificial Sequence
```

```
<220> FEATURE:
<223> OTHER INFORMATION: Primer COVID19-S-C27-NheI-R1

<400> SEQUENCE: 13
ctagctagct tagcccttca ggcaggaaca gcag                                        34

<210> SEQ ID NO 14
<211> LENGTH: 27
<212> TYPE: DNA
<213> ORGANISM: Artificial Sequence
<220> FEATURE:
<223> OTHER INFORMATION: Primer COVID19-S-C53-XhoI-F1

<400> SEQUENCE: 14
ccgctcgaga tgttcgtgtt tctggtg                                                27

<210> SEQ ID NO 15
<211> LENGTH: 32
<212> TYPE: DNA
<213> ORGANISM: Artificial Sequence
<220> FEATURE:
<223> OTHER INFORMATION: Primer COVID19-S-C53-NheI-R1

<400> SEQUENCE: 15
ctagctagct tagaagccca gccagatgta cc                                          32

<210> SEQ ID NO 16
<211> LENGTH: 27
<212> TYPE: DNA
<213> ORGANISM: Artificial Sequence
<220> FEATURE:
<223> OTHER INFORMATION: Primer COVID19-S-C19HA-XhoI-F1

<400> SEQUENCE: 16
ccgctcgaga tgttcgtgtt tctggtg                                                27

<210> SEQ ID NO 17
<211> LENGTH: 63
<212> TYPE: DNA
<213> ORGANISM: Artificial Sequence
<220> FEATURE:
<223> OTHER INFORMATION: Primer COVID19-S-C19HA-NheI-R1

<400> SEQUENCE: 17
ctagctagct taggcataat ctggcacatc ataagggtaa cagcagcttc cacaagaaca          60
gca                                                                         63

<210> SEQ ID NO 18
<211> LENGTH: 30
<212> TYPE: DNA
<213> ORGANISM: Artificial Sequence
<220> FEATURE:
<223> OTHER INFORMATION: Primer SARS-COV-S-C19-XhoI-F1

<400> SEQUENCE: 18
ccgctcgaga tgttcatctt tctgctgttc                                            30

<210> SEQ ID NO 19
<211> LENGTH: 33
<212> TYPE: DNA
<213> ORGANISM: Artificial Sequence
<220> FEATURE:
<223> OTHER INFORMATION: Primer SARS-COV-S-C19-NheI-R1

<400> SEQUENCE: 19
```

-continued

```
ctagctagct taacagcaag atccacagga gca                                    33

<210> SEQ ID NO 20
<211> LENGTH: 28
<212> TYPE: DNA
<213> ORGANISM: Artificial Sequence
<220> FEATURE:
<223> OTHER INFORMATION: Primer MERS-CoV-S-C19-XhoI-F1

<400> SEQUENCE: 20
ccgctcgaga tgatacactc agtgtttc                                          28

<210> SEQ ID NO 21
<211> LENGTH: 31
<212> TYPE: DNA
<213> ORGANISM: Artificial Sequence
<220> FEATURE:
<223> OTHER INFORMATION: Primer MERS-CoV-S-C19-NheI-R1

<400> SEQUENCE: 21
ctagctagct taattacact taagttttcc c                                      31
```